US008492364B2

(12) United States Patent
Pier et al.

(10) Patent No.: US 8,492,364 B2
(45) Date of Patent: Jul. 23, 2013

(54) METHODS AND COMPOSITIONS RELATING TO SYNTHETIC β-1,6 GLUCOSAMINE OLIGOSACCHARIDES

(75) Inventors: Gerald B. Pier, Brookline, MA (US); Nikolay Nifantiev, Moscow (RU); Yury Tsvetkov, Moscow (RU); Marina Gening, Moscow (RU)

(73) Assignee: The Brigham and Women's Hospital, Inc., Boston, MA (US)

( * ) Notice: Subject to any disclaimer, the term of this patent is extended or adjusted under 35 U.S.C. 154(b) by 46 days.

(21) Appl. No.: 13/055,178

(22) PCT Filed: Jul. 21, 2009

(86) PCT No.: PCT/US2009/004206
§ 371 (c)(1),
(2), (4) Date: Mar. 2, 2011

(87) PCT Pub. No.: WO2010/011284
PCT Pub. Date: Jan. 28, 2010

(65) Prior Publication Data
US 2011/0150880 A1    Jun. 23, 2011

Related U.S. Application Data

(60) Provisional application No. 61/135,493, filed on Jul. 21, 2008, provisional application No. 61/208,155, filed on Feb. 20, 2009.

(51) Int. Cl.
*A61K 31/70* (2006.01)

(52) U.S. Cl.
USPC ............................................................ 514/62

(58) Field of Classification Search
None
See application file for complete search history.

(56) References Cited

U.S. PATENT DOCUMENTS

| | | |
|---|---|---|
| 2,842,049 A | 7/1958 | Delangre |
| 4,197,290 A | 4/1980 | Yoshida |
| 4,285,936 A | 8/1981 | Pier et al. |
| 4,379,145 A | 4/1983 | Masuho et al. |
| 4,443,549 A | 4/1984 | Sadowski |
| 4,465,776 A | 8/1984 | Cidlowski et al. |
| 4,578,458 A | 3/1986 | Pier |
| 4,652,448 A | 3/1987 | Sadowski |
| 4,755,381 A | 7/1988 | Cryz |
| 4,786,592 A | 11/1988 | Deal et al. |
| 4,789,735 A | 12/1988 | Frank et al. |
| 4,795,803 A | 1/1989 | Lindberg et al. |
| 4,830,852 A | 5/1989 | Marburg et al. |
| 4,859,449 A | 8/1989 | Mattes |
| 4,879,272 A | 11/1989 | Shimoda et al. |
| 4,902,616 A | 2/1990 | Fournier et al. |
| 5,055,455 A | 10/1991 | Pier |
| 5,362,754 A | 11/1994 | Raad et al. |
| 5,366,505 A | 11/1994 | Farber |
| 5,425,946 A | 6/1995 | Tai et al. |
| 5,571,511 A | 11/1996 | Fischer |
| 5,589,591 A | 12/1996 | Lewis |
| 5,688,516 A | 11/1997 | Raad et al. |
| 5,718,694 A | 2/1998 | Rupp |
| 5,763,191 A | 6/1998 | Knoll et al. |
| 5,830,539 A | 11/1998 | Yan et al. |
| 5,858,350 A | 1/1999 | Vournakis et al. |
| 5,866,140 A | 2/1999 | Fattom et al. |
| 5,872,215 A | 2/1999 | Osbourne et al. |
| 5,980,910 A | 11/1999 | Pier |
| 5,989,542 A | 11/1999 | Pier et al. |
| 6,235,883 B1 | 5/2001 | Jakobovits et al. |
| 6,245,735 B1 | 6/2001 | Pier |
| 6,399,066 B1 | 6/2002 | Pier |
| 6,743,431 B2 | 6/2004 | Pier |
| 6,903,194 B1 | 6/2005 | Sato et al. |
| 6,924,360 B2 | 8/2005 | Green et al. |
| 7,157,443 B2 | 1/2007 | Joyce et al. |
| 7,252,828 B2 | 8/2007 | Pier et al. |
| 7,550,569 B2 | 6/2009 | Baker et al. |
| 7,723,087 B2 | 5/2010 | Pier et al. |
| 7,786,255 B2 | 8/2010 | Pier et al. |
| 2001/0048929 A1 | 12/2001 | Chong et al. |
| 2002/0031528 A1 | 3/2002 | Fattom |
| 2002/0119166 A1 | 8/2002 | Pier et al. |
| 2003/0124631 A1 | 7/2003 | Pier et al. |
| 2004/0005632 A1 | 1/2004 | Erlanson et al. |
| 2004/0091494 A1 | 5/2004 | Pier et al. |
| 2004/0175731 A1 | 9/2004 | Pier et al. |
| 2005/0025775 A1 | 2/2005 | Pier et al. |
| 2005/0118198 A1 | 6/2005 | Pier et al. |
| 2006/0115486 A1 | 6/2006 | Pier et al. |
| 2009/0162341 A1 | 6/2009 | Foster et al. |
| 2010/0021503 A1 | 1/2010 | Denoel et al. |
| 2010/0303852 A1 | 12/2010 | Biemans et al. |
| 2010/0322959 A1 | 12/2010 | Biemans et al. |
| 2011/0008385 A1 | 1/2011 | Castado et al. |

FOREIGN PATENT DOCUMENTS

| | | |
|---|---|---|
| CN | 01136484 | 4/2002 |
| CN | 1344722 A | 4/2002 |

(Continued)

OTHER PUBLICATIONS

EBI Dbfetch Submission; EMBL-EBI; Accession No. U43366; Heilmann et al., Apr. 17, 2005 (last submission).
GenBank Submission; NIH/BCBI; Accession No. AAZ87998; Pier et al; May 31, 2000.
[No Author Listed] Adis R&D Profile Drug in R&D. Adis International. 2003;4(6):383-5. Available at http://www.ingentaconnect.com/content/adis/rdd//2003/00000004/00000006/art00013. Last accessed Nov. 11, 2010. Abstract only.
Allignet et al., Tracking adhesion factors in *Staphylococcus caprae* strains responsible for human bone infections following implantation of orthopaedic material. Microbiology. Aug. 1999;145 (Pt 8):2033-42.

(Continued)

*Primary Examiner* — Craig Ricci
(74) *Attorney, Agent, or Firm* — Wolf, Greenfield & Sacks, P.C.

(57) ABSTRACT

The invention relates to the compositions of synthetic oligo-β-(1→6)-2-amino-2-deoxy-D-glucopyranosides conjugated to carriers, and methods for making and use same.

10 Claims, 22 Drawing Sheets

FOREIGN PATENT DOCUMENTS

| | | |
|---|---|---|
| EP | 0 302 781 A1 | 2/1989 |
| EP | 0 574 000 A1 | 12/1993 |
| EP | 0 694 309 A2 | 10/1996 |
| FR | 2 410 043 A1 | 6/1979 |
| FR | 2 581 877 A1 | 11/1986 |
| FR | 2 640 628 A1 | 6/1990 |
| GB | 2 009 771 A | 6/1979 |
| WO | WO 85/05037 A1 | 11/1985 |
| WO | WO 86/02358 A1 | 4/1986 |
| WO | WO 88/02028 A1 | 3/1988 |
| WO | WO 89/04873 A1 | 6/1989 |
| WO | WO 90/03398 A1 | 4/1990 |
| WO | WO 90/06696 A2 | 6/1990 |
| WO | WO 93/01276 A1 | 1/1993 |
| WO | WO 93/09811 A1 | 5/1993 |
| WO | WO 93/19373 A1 | 9/1993 |
| WO | WO 94/15640 A1 | 7/1994 |
| WO | WO 97/17334 A1 | 5/1997 |
| WO | WO 97/19105 A1 | 5/1997 |
| WO | WO 98/47915 A1 | 10/1998 |
| WO | WO 98/52605 A1 | 11/1998 |
| WO | WO 99/40440 A1 | 8/1999 |
| WO | WO 00/03745 A2 | 1/2000 |
| WO | WO 00/35504 A1 | 6/2000 |
| WO | WO 00/56360 A2 | 9/2000 |
| WO | WO 03/053462 A2 | 7/2003 |
| WO | WO 03/061558 A2 | 7/2003 |
| WO | WO 03/085093 A2 | 10/2003 |
| WO | WO 03/087054 A2 | 10/2003 |
| WO | WO 2004/043405 A2 | 5/2004 |
| WO | WO 2004/043407 A2 | 5/2004 |
| WO | WO 2004/080490 A2 | 9/2004 |
| WO | WO 2005/000346 A1 | 1/2005 |
| WO | WO 2005/103084 A2 | 11/2005 |
| WO | WO 2006/032472 A2 | 3/2006 |
| WO | WO 2006/065503 A2 | 6/2006 |
| WO | WO 2006/065553 A2 | 6/2006 |
| WO | WO 2007/113223 A2 | 10/2007 |
| WO | WO 2007/113224 A2 | 10/2007 |

OTHER PUBLICATIONS

Ammendolia et al., Slime production and expression of the slime-associated antigen by Staphylococcal clinical isolates. J Clin Microbiol. Oct. 1999;37(10):3235-8.

Arciola et al., In catheter infections by Staphylococcus epidermidis the intercellular adhesion (ica) locus is a molecular marker of the virulent slime-producing strains. J Biomed Mater Res. Mar. 5, 2002;59(3):557-62. Abstract Only.

Baldassarri et al., Purification and characterization of the Staphylococcal slime-associated antigen and its occurrence among Staphylococcus epidermis clinical isolates. Infect Immun. Aug. 1996;64(8):3410-5.

Barsham et al., Detection of antibodies to Staphylococcus epidermidis in infected total hip replacements by an enzyme linked immunosorbent assay. J Clin Pathol. Jul. 1985;38(7):839-40.

Bhasin et al., Identification of a gene essential for O-acetylation of the Staphylococcus aureus type 5 capsular polysaccharide. Mol Microbiol. Jan. 1998;27(1):9-21. Abstract Only.

Burgeot et al., Immunopotentiation of Staphylococcus aureus type 5 capsular polysaccharide co-entrapped in liposomes with alpha-toxin. Vaccine. Feb. 28, 2001;19(15-16):2092-9. Abstract only.

Capek et al., Chapters 22: Carbohydrates and Chapter 23: Polysaccharides. In: Journal of Chromatography Journal Library, vol. 3: Liquid Column Chromatography, A Survey of Modern Technicques and Applications. Deyl et al., eds. Elsevier Scientific Publishing Company: New York, 1975:465-528.

Cerca et al., Comparative antibody-mediated phagocytosis of Staphylococcus epidermidis cells grown in a biofilm or in the planktonic state. Infect Immun. Aug. 2006;74(8):4849-55.

Cerca et al., Influence of batch or fed-batch growth on Staphylococcus epidermidis biofilm formation. Lett Appl Microbiol. 2004;39(5):420-4.

Cerca et al., Molecular basis for preferential protective efficacy of antibodies directed to the poorly acetylated form of Staphylococcal poly-N-acetyl-beta-(1-6)-glucosamine. Infect Immun. Jul. 2007;75(7):3406-13. Epub Apr. 30, 2007.

Cerca et al., Protection against Escherichia coli infection by antibody to the Staphylococcus aureus poly-N-acetylglucosamine surface polysaccharide. Proc Natl Acad Sci U S A. May 1, 2007;104(18):7528-33. Epub Apr. 19, 2007.

Christensen et al., Adherence of slime-producing strains of Staphylococcus epidermidis to smooth surfaces. Infect Immun. Jul. 1982;37(1):318-26.

Chu et al., Preparation, characterization, and immunogenicity of conjugates composed of the O-specific polysaccharide of Shigella dysenteriae type 1 (Shiga's bacillus) bound to tetanus toxoid. Infect Immun. Dec. 1991;59(12):4450-8.

Cramton et al., Anaerobic conditions induce expression of polysaccharide intercellular adhesin in Staphylococcus aureus and Staphylococcus epidermidis. Infect Immun. Jun. 2001;69(6):4079-85.

Cramton et al., The intercellular adhesion (ica) locus is present in Staphylococcus aureus and is required for biofilm formation. Infect Immun. Oct. 1999;67(10):5427-33.

Dobrin, et al., The role of complement, immunoglobulin and bacterial antigen in coagulase-negative Staphylococcal shunt nephritis. Am J Med. Nov. 1975;59(5):660-73. Abstract only.

Elder et al., Characterization of monoclonal antibodies specific for adhesion: isolation of an adhesin in Streptococcus sanguis FW213. Infect Immun. Nov. 1986;54(2):421-7.

Espersen, et al., Enzyme-linked immunosorbent assay for detection of Staphylococcus epidermidis antibody in experimental S. epidermidis endocarditis. J Clin Microbiol. Feb. 1986;23(2):339-42.

Espersen, et al., Solid-phase radioimmunoassay for IgG antibodies to Staphylococcus epidermidis. Use in serious coagulase-negative Staphylococcal infections. Arch Intern Med. Apr. 1987;147(4):689-93. Abstract only.

Fattom et al., Antigenic determinants of Staphylococcus aureus type 5 and type 8 capsular polysaccharide vaccines. Infect Immun. Oct. 1998;66(10):4588-92.

Fattom et al., Comparative immunogenicity of conjugates composed of the Staphylococcus aureus type 8 capsular polysaccharide bound to carrier proteins by adipic acid dihydrazide or N-succinimidyl-3-(2-pyridyldithio)propionate. Infect Immun. Feb. 1992;60(2):584-9.

Fattom et al., Development of StaphVAX, a polysaccharide conjugate vaccine against S. aureus infection: from the lab bench to phase III clinical trials. Vaccine. Feb. 17, 2004;22(7):880-7. Abstract only.

Fattom et al., Effect of conjugation methodology, carrier protein, and adjuvants on the immune response to Staphylococcus aureus capsular polysaccharides. Vaccine. Oct. 1995;13(14):1288-93.

Fattom et al., Synthesis and immunologic properties in mice of vaccines composed of Staphylococcus aureus type 5 and type 8 capsular polysaccharides conjugated to Pseudomonas aeruginosa exotoxin A. Infect Immun. Jul. 1990;58(7):2367-74.

Ferreiros et al., Purification and partial characterization of a K99-antigen associated adhesin in Escherichia coli (637 strain). Rev Esp Fisiol. Mar. 1983;39(1):45-50.

Fey et al., Characterization of the relationship between polysaccharide intercellular adhesin and hemagglutination in Staphylococcus epidermidis. J Infect Dis. Jun. 1999;179(6):1561-4. Abstract Only.

Fitzpatrick et al., Environmental regulation of biofilm formation in intensive care unit isolates of Staphylococcus epidermidis. J Hosp Infect. Nov. 2002;52(3):212-8.

Fournier et al., Purification and characterization of Staphylococcus aureus type 8 capsular polysaccharide. Infect Immun. Jul. 1984;45(1):87-93.

Fowler et al., The intercellular adhesin locus ica is present in clinical isolates of Staphylococcus aureus from bacteremic patients with infected and uninfected prosthetic joints. Med Microbiol Immunol (Berl). Apr. 2001;189(3):127-31. Abstract Only.

Fridman et al., One-pot synthesis of glucosamine oligosaccharides. Org Lett. Jan. 24, 2002;4(2):281-3.

Gelosia et al., Phenotypic and genotypic markers of Staphylococcus epidermidis virulence. Clin Microbiol Infect. Apr. 2001;7(4):193-9. Abstract Only.

Gening et al., Synthesis of beta-(1→6)-linked glucosamine oligosaccharides corresponding to fragments of the bacterial surface polysaccharide poly-N-acetylglucosamine. Carbohydr Res. Feb. 26, 2007;342(3-4):567-75. Epub Sep. 6, 2006.

Gening et al., Synthetic {beta}-(1->6)-linked N-acetylated and nonacetylated oligoglucosamines used to produce conjugate vaccines for bacterial pathogens. Infect Immun. Feb. 2010;78(2):764-72. Epub Nov. 30, 2009.

Gening et al., The study of the reaction of terminated oligomerization in the synthesis of oligo-(beta1-6)-glucosamines. Bioorg Khim. Jul.-Aug. 2006;32(4):432-43. Published in English in Russian Journal of Biorganic Chemistry, 2006;32(4):389-99.

Gerke et al., Characterization of the N-acetylglucosaminyltransferase activity involved in the biosynthesis of the *Staphylococcus epidermidis* polysaccharide intercellular adhesin. J Biol Chem. Jul. 17, 1998;273(29):18586-93.

Götz, *Staphylococcus* and biofilms. Mol Microbiol. Mar. 2002;43(6):1367-78.

Grachev et al., NMR and conformational studies of linear and cyclic oligo-(1→6)-β-D-glucosamines. Carbohydr Res. Nov. 8, 2011;346(15):2499-510. Epub Sep. 5, 2011.

Gray et al., Effect of extracellular slime substance from *Staphylococcus epidermidis* on the human cellular immune response. Lancet. Feb. 18, 1984;1(8373):365-7.

Heilmann et al., Molecular basis of intercellular adhesion in the biofilm-forming *Staphylococcus epidermidis*. Mol Microbiol. Jun. 1996;20(5):1083-91.

Hogt et al., Cell surface characteristics of coagulase-negative *Staphylococci* and their adherence to fluorinated poly(ethylenepropylene). Infect Immun. Jan. 1986;51(1):294-301.

Ichiman et al., Induction of resistance with heat-killed unencapsulated strains of *Staphylococcus epidermidis* against challenge with encapsulated strains of *Staphylococcus epidermidis*. Microbiol Immunol. 1989;33(4):277-86.

Ichiman et al., Relation of human serum antibody against *Staphylococcus epidermidis* cell surface polysaccharide detected by enzyme-linked immunosorbent assay to passive protection in the mouse. J Appl Bacteriol. Aug. 1991;71(2):176-81.

Ichiman et al., Specificity of monoclonal antibodies against an encapsulated strain of *Staphylococcus epidermidis*. in the *Staphylococci*, Zbl Bakt. 1991;Suppl 21:150-2.

Ichiman et al., The relationship of capsular-type of *Staphylococcus epidermidis* to virulence and induction of resistance in the mouse. J Appl Bacteriol. Oct. 1981;51(2):229-41.

Jefferson et al., Identification of a 5-nucleotide sequence that controls expression of the ica locus in *Staphylococcus aureus* and characterization of the DNA-binding properties of IcaR. Mol Microbiol. May 2003;48(4):889-99.

Jefferson et al., The teicoplanin-associated locus regulator (TcaR) and the intercellular adhesin locus regulator (IcaR) are transcriptional inhibitors of the ica locus in *Staphylococcus aureus*. J Bacteriol. Apr. 2004;186(8):2449-56.

Ji et al., Identification of critical *Staphylococcal* genes using conditional phenotypes generated by antisense RNA. Science. Sep. 21, 2001;293(5538):2266-9.

Ji et al., Regulated antisense RNA eliminates alpha-toxin virulence in *Staphylococcus aureus* infection. J Bacteriol. Nov. 1999;181(21):6585-90.

Johnson et al., Interference with granulocyte function by *Staphylococcus epidermidis* slime. Infect Immun. Oct. 1986;54(1):13-20.

Jones, Revised structures for the capsular polysaccharides from *Staphylococcus aureus* Types 5 and 8, components of novel glycoconjugate vaccines. Carbohydr Res. May 2, 2005;340(6):1097-106. Abstract only.

Joyce et al., Isolation, structural characterization, and immunological evaluation of a high-molecular-weight exopolysaccharide from *Staphylococcus aureus*. Carbohydr Res. Apr. 22, 2003;338(9):903-22.

Kelly-Quintos et al., Biological Characterization of Fully Human Monoclonal Antibodies to *Staphylococcal* Surface Polysaccharide PNAG. Abstracts of the 104th General Meeting of the American Society for Microbiology. Am Soc Microbiol. May 2004. Abstract A-63. Abstract and corresponding presentation.

Kelly-Quintos et al., Characterization of the opsonic and protective activity against *Staphylococcus aureus* of fully human monoclonal antibodies specific for the bacterial surface polysaccharide poly-N-acetylglucosamine. Infect Immun. May 2006;74(5):2742-50.

Kelly-Quintos et al., The role of epitope specificity in the human opsonic antibody response to the *Staphylococcal* surface polysaccharide poly N-acetyl glucosamine. J Infect Dis. Dec. 1, 2005;192(11):2012-9. Epub Nov. 1, 2005.

Keutmann et al., Evidence for a conformational change in deglycosylated glycoprotein hormones. FEBS Lett. Jun. 17, 1985;185(2):333-8.

Kille et al., Sucralose: assessment of teratogenic potential in the rat and the rabbit. Food Chem Toxicol. 2000;38 Suppl 2:S43-52.

Klevens et al., Invasive methicillin-resistant *Staphylococcus aureus* infections in the United States. JAMA. Oct. 17, 2007;298(15):1763-71.

Kohler, Derivation and diversification of monoclonal antibodies. Science. Sep. 19, 1986;233(4770):1281-6.

Kojima et al., Antibody to the capsular polysaccharide/adhesin protects rabbits against catheter-related bacteremia due to coagulase-negative *Staphylococci*. J Infect Dis. Aug. 1990:162(2):435-41.

Kolberg et al., Monoclonal antibodies with specificities for *Streptococcus pneumoniae* group 9 capsular polysaccharides. FEMS Immunol Med Microbiol. Apr. 1998;20(4):249-55. Abstract Only.

Kossaczka et al., Synthesis and immunological properties of Vi and di-O-acetyl pectin protein conjugates with adipic acid dihydrazide as the linker. Infect Immun. Jun. 1997;65(6):2088-93.

Kropec et al., Poly-N-acetylglucosamine production in *Staphylococcus aureus* is essential for virulence in murine models of systemic infection. Infect Immun. Oct. 2005;73(10):6868-76.

Lee et al., Chemical characterization and immunogenicity of capsular polysaccharide isolated from mucoid *Staphylococcus aureus*. Infect Immun. Sep. 1987;55(9):2191-7.

Lee et al., Effect of a trivalent vaccine against *Staphylococcus aureus* mastitis lymphocyte subpopulations, antibody production, and neutrophil phagocytosis. Can J Vet Res. Jan. 2005;69(1):11-8.

Leith et al., Purification of a Mycoplasma pneumoniae adhesin by monoclonal antibody affinity chromatography. J Bacteriol. Feb. 1984;157(2):678-80.

Leung et al., Efficient synthesis and protein conjugation of beta-(1→6)-D-N-acetylglucosamine oligosaccharides from the polysaccharide intercellular adhesin. Carbohydr Res. Mar. 31, 2009;344(5):570-5. Epub Jan. 3, 2009.

Longworth et al., O-Acetylation status of the capsular polysaccharides of serogroup Y and W135 meningococci isolated in the UK. FEMS Immunol Med Microbiol. Jan. 14, 2002;32(2):119-23. Abstract Only.

Ludwicka et al., Investigation on extracellular slime substance produced by *Staphylococcus epidermidis*. Zentralbl Bakteriol Mikrobiol Hyg [A]. Dec. 1984;258(2-3):256-67.

Mack et al., Association of biofilm production of coagulase-negative *Staphylococci* with expression of a specific polysaccharide intercellular adhesin. J Infect Dis. Oct. 1996;174(4):881-4.

Mack et al., Characterization of transposon mutants of biofilm-producing *Staphylococcus epidermidis* impaired in the accumulative phase of biofilm production: genetic identification of a hexosamine-containing polysaccharide intercellular adhesin. Infect Immun. Aug. 1994;62(8):3244-53.

Mack et al., Essential functional role of the polysaccharide intercellular adhesin of *Staphylococcus epidermidis* in hemagglutination. Infect Immun. Feb. 1999;67(2):1004-8.

Mack et al., Genetic and biochemical analysis of *Staphylococcus epidermidis* biofilm accumulation. Methods Enzymol. 2001;336:215-39.

Mack et al., Identification of three essential regulatory gene loci governing expression of *Staphylococcus epidermidis* polysaccharide intercellular adhesin and biofilm formation. Infect Immun. Jul. 2000;68(7):3799-807.

Mack et al., Molecular mechanisms of *Staphylococcus epidermidis* biofilm formation. J Hosp Infect. Dec. 1999;43 Suppl:S113-25. Abstract Only.

Mack et al., Parallel induction by glucose of adherence and a polysaccharide antigen specific for plastic-adherent *Staphylococcus epidermidis*: evidence for functional relation to intercellular adhesion. Infect Immun. May 1992;60(5):2048-57.

Mack et al., The intercellular adhesin involved in biofilm accumulation of *Staphylococcus epidermidis* is a linear beta-1,6-linked glucosaminoglycan: purification and structural analysis. J Bacteriol. Jan. 1996;178(1):175-83.

Maira-Litran et al., Biologic properties and vaccine potential of the *Staphylococcal* poly-N-acetyl glucosamine surface polysaccharide. Vaccine. Feb. 17, 2004;22(7):872-9. Review.

Maira-Litran et al., Comparative opsonic and protective activities of *Staphylococcus aureus* conjugate vaccines containing native or deacetylated *Staphylococcal* Poly-N-acetyl-beta-(1-6)-glucosamine. Infect Immun. Oct. 2005;73(10):6752-62. Erratum: Infect Immun. Nov. 2005;73(11):7789.

Maira-Litran et al., Deacetylated-poly-N-acetyl Glucosamine (dPNAG) Polysaccharide Conjugated to Diphtheria Toxoid (DT) Confers Protection Against Multiple Strains of *Staphylococcus aureus* in a Murine Model of Bacteremia. Abstracts of the 104th General Meeting of the American Society for Microbiology. Am Soc Microbiol. May 2004. Abstract D-130. Abstract and corresponding presentation.

Maira-Litran et al., Immunochemical properties of the *Staphylococcal* poly-N-acetylglucosamine surface polysaccharide. Infect Immun. Aug. 2002;70(8):4433-40.

Maira-Litran et al., Relationship Between the Polysacharide Intercellular Adhesin (PIA) and Poly-N-Succinyl b-1-6 Glucosamine (PNSG) Molecules Produced by Pathogenic *Staphylococi*. In: Abstracts of the General Meeting of the American Society for Microbiology. Session No. 31/D. May 2001:283-4. Abstract No. D42.

Maira-Litran et al., Synthesis and Immunological Properties of a *Staphylococcal* Deacetylated-poly-N-acetyl Glucosamine (dPNAG) Polysaccharide and Clumping Factor A (ClfA) Protein Conjugate Vaccine. Abstracts of the 104th General Meeting of the American Society for Microbiology. Am Soc Microbiol. May 2004. Abstract E-062. Abstract and corresponding presentation.

McKenney et al., Broadly protective vaccine for *Staphylococcus aureus* based on an in vivo-expressed antigen. Science. May 28, 1999;284(5419):1523-7.

McKenney et al., The ica locus of *Staphylococcus epidermidis* encodes production of the capsular polysaccharide/adhesin. Infect Immun. Oct. 1998;66(10):4711-20.

McKenney et al., Vaccine potential of poly-1-6 beta-D-N-succinylglucosamine, an immunoprotective surface polysaccharide of *Staphylococcus aureus* and *Staphylococcus epidermidis*. J Biotechnol. Sep. 29, 2000;83(1-2):37-44.

McNeely et al., Antibody responses to capsular polysaccharide backbone and O-acetate side groups of *Streptococcus pneumoniae* type 9V in humans and rhesus macaques. Infect Immun. Aug. 1998;66(8):3705-10.

Melean et al., Toward the automated solid-phase synthesis of oligoglucosamines: systematic evaluation of glycosyl phosphate and glycosyl trichloroacetimidate building blocks. Carbohydr Res. Nov. 19, 2002;337(21-23):1893-916.

Michon et al., Structure activity studies on group C meningococcal polysaccharide-protein conjugate vaccines: effect of O-acetylation on the nature of the protective epitope. Dev Biol (Basel). 2000;103:151-60. Abstract Only.

Moch et al., Isolation and characterization of the alpha-sialyl-beta-2,3-galactosyl-specific adhesin from fimbriated *Escherichia coli*. Proc Natl Acad Sci U S A. May 1987;84(10):3462-6.

Moreau et al., Structure of the type 5 capsular polysaccharide of *Staphylococcus aureus*. Carbohydr Res. Jul. 1, 1990;201(2):285-97.

Muller et al., Capsular polysaccharide/adhesin (PS/A) production by coagulase-negative *Staphylococci* (CNS) is associated with adherence to silastic tubing. 1989:49. Abstract B-111.

Muller et al., Occurrence of capsular polysaccharide/adhesin among clinical isolates of coagulase-negative *Staphylococci*. J Infect Dis. Nov. 1993;168(5):1211-8.

Nagy et al., Multi-adhesin vaccines for the protection of the neonatal piglet against "*E. coli*" infections. Dev Biol Stand. 1983;53:189-97.

O'Brien et al., Production of antibodies to *Staphylococcus aureus* serotypes 5, 8, and 336 using poly(DL-lactide-co-glycolide) microspheres. J Dairy Sci. Aug. 2000;83(8):1758-66. Abstract only.

O'Gara et al., *Staphylococcus epidermidis* biofilms: importance and implications. J Med Microbiol. Jul. 2001;50(7):582-7.

Ohshima et al., Cell surface antigen of encapsulated *Staphylococcus epidermidis* ATCC 31432. J Clin Microbiol. Jul. 1987;25(7):1338-40.

Ohshima et al., Immunochemical characterization and biological properties of a cell surface antigen extracted from encapsulated *Staphylococcus epidermidis* strain SE-10. Zentralbl Bakteriol 1990;274:417-25.

Ohshima et al., Protection inducing antigen of an encapsulated *Staphylococcus epidermis* SE-10. in the *Staphylococci*, Zbl Bakt. 1991;Suppl 21:279-80.

Peterson et al., The key role of peptidoglycan in the opsonization of *Staphylococcus aureus*. J Clin Invest. Mar. 1978;61(3):597-609.

Pier et al., Further purification and characterization of high-molecular-weight polysaccharide from *Pseudomonas aeruginosa*. Infect Immun. Dec. 1983;42(3):936-41.

Pier et al., Isolation and characterization of a high-molecular-weight polysaccharide from the slime of *Pseudomonas aeruginosa*. Infect Immun. Dec. 1978;22(3):908-18.

Pier et al., Protective immunity induced in mice by immunization with high-molecular-weight polysaccharide from *Pseudomonas aeruginosa*. Infect Immun. Dec. 1978;22(3):919-25.

Preston et al., Production and characterization of a set of mouse-human chimeric immunoglobulin G (IgG) subclass and IgA monoclonal antibodies with identical variable regions specific for *Pseudomonas aeruginosa* serogroup O6 lipopolysaccharide. Infect Immun. Sep. 1998;66(9):4137-42.

Preston et al., Prophylactic and therapeutic efficacy of immunoglobulin G antibodies to *Pseudomonas aeruginosa* lipopolysaccharide against murine experimental corneal infection. Invest Ophthalmol Vis Sci. Jun. 1997;38(7):1418-25.

Propst et al., Abstracts of the General Meeting of the American Society for Microbiology. 1998;42:242. Abstract only. 2 pages.

Quie et al., Coagulase-negative *Staphylococcal* adherence and persistence. J Infect Dis. Oct. 1987;156(4):543-7.

Rogemond et al., Lectinlike adhesins in the *Bacteroides fragilis* group. Infect Immun. Jul. 1986;53(1):99-102.

Rupp et al., Characterization of *Staphylococcus epidermidis* polysaccharide intercellular adhesin/hemagglutinin in the pathogenesis of intravascular catheter-associated infection in a rat model. Infect Immun. May 1999;67(5):2656-9.

Rupp et al., Characterization of the importance of polysaccharide intercellular adhesin/hemagglutinin of *Staphylococcus epidermidis* in the pathogenesis of biomaterial-based infection in a mouse foreign body infection model. Infect Immun. May 1999;67(5):2627-32.

Sanford et al., Detection of *Staphylococcal* membrane receptors on virus-infected cells by direct adhesin overlay. Infect Immun. Jun. 1986;52(3):671-5.

Schumacher-Perdreau et al., Comparative analysis of a biofilm-forming *Staphylococcus epidermidis* strain and its adhesion-positive, accumulation-negative mutant M7. FEMS Microbiol Lett. Mar. 15, 1994;117(1):71-8.

Skurnik et al., Animal and human antibodies to distinct *Staphylococcus aureus* antigens mutually neutralize opsonic killing and protection in mice. J Clin Invest. Sep. 1, 2010;120(9):3220-33.

Soell et al., Capsular polysaccharide types 5 and 8 of *Staphylococcus aureus* bind specifically to human epithelial (KB) cells, endothelial cells, and monocytes and induce release of cytokines. Infect Immun. Apr. 1995;63(4):1380-6.

Sompolinsky et al., Encapsulation and capsular types in isolates of *Staphylococcus aureus* from different sources and relationship to phage types. J Clin Microbiol. Nov. 1985;22(5):828-34.

Takeda et al., Protection against endocarditis due to *Staphylococcus epidermidis* by immunization with capsular polysaccharide/adhesin. Circulation. Dec. 1991;84(6):2539-46.

Thoma et al., Synthesis of oligosaccharide-polylysine conjugates: A well characterized sialyl lewis polymer for elisa. J Am Chem Soc. 1997;119(31):7414-5.

Thomas et al., Enzyme-linked lectinsorbent assay measures N-acetyl-D-glucosamine in matrix of biofilm produced by *Staphylococcus epidermidis*. Curr Microbiol. Oct. 1997;35(4):249-54.

Tojo et al., Isolation and characterization of a capsular polysaccharide adhesin from *Staphylococcus epidermidis*. J Infect Dis. Apr. 1988;157(4):713-22.

Tollersrud et al., Genetic and serologic evaluation of capsule production by bovine mammary isolates of *Staphylococcus aureus* and other *Staphylococcus* spp. from Europe and the United States. J Clin Microbiol. Aug. 2000;38(8):2998-3003.

Vershigora et al., Secretory antibodies to homologous and heterologous *Staphylococcal* strains in the colostrum of rabbits. Zh Mikrobiol Epidemiol Immunobiol. 1980;88-90. Russian. 1 page.

Von Eiff et al., Distribution of capsular and surface polysaccharide serotypes of *Staphylococcus aureus*. Diagn Microbiol Infect Dis. Jul. 2007;58(3):297-302. Epub Mar. 26, 2007.

Vuong et al., A crucial role for exopolysaccharide modification in bacterial biofilm formation, immune evasion, and virulence. J Biol Chem. Dec. 24, 2004;279(52):54881-6. Epub Oct. 22, 2004.

Wessels et al., Isolation and characterization of type IV group B *Streptococcus* capsular polysaccharide. Infect Immun. Apr. 1989;57(4):1089-94.

Wessels et al., Structural properties of group B *Streptococcal* type III polysaccharide conjugate vaccines that influence immunogenicity and efficacy. Infect Immun. May 1998;66(5):2186-92.

Wicken et al., Characterization of group N *Streptococcus* lipoteichoic acid. Infect Immun. May 1975;11(5):973-81.

Wray et al., Identification and characterization of a uroepithelial cell adhesin from a uropathogenic isolate of *Proteus mirabilis*. Infect Immun. Oct. 1986;54(1):43-9.

Yamada, et al., Possible common biological and immunological properties for detecting encapsulated strains of *Staphylococcus epidermidis*. J Clin Microbiol. Oct. 1988;26(10):2167-72.

Yang et al., A practical synthesis of a (1—>6)-linked beta-D-glucosamine nonasaccharide. Carbohydr Res. Mar. 14, 2003;338(6):495-502.

Yang et al., Synthesis of (1-6)-β-D-glucosamine hexasaccharide, a potential antitumor and immunostimulating agent. Tetrahedron Lett. Oct. 2002;43:7561-3.

Yang et al., Synthesis of biantennary beta-D-(1→6) glucosamine oligosaccharides. Carbohydr Res. Jun. 16, 2003;338(12):1313-8.

Yoshida et al., Cross protection between a strain of *Staphylococcus epidermidis* and eight other species of coagulase-negative *Staphylococci*. Can J Microbiol. Jul. 1988;34(7):913-5.

Yoshida et al., Mouse virulent strain of *Staphylococcus epidermidis*. Relation of antiphagocytic activity to the protection-inducing antigen. Jpn J Microbiol. Jun. 1976;20(3):209-17.

Yoshida et al., Immunological response to a strain of *Staphylococcus epidermidis* in the rabbit: production of protective antibody. J Med Microbiol. Nov. 1978;11(4):371-7. Abstract only.

Youmans, *Staphylococci*, *Staphylococcal* Disease, and Toxic Shock Syndrome. In: The Biologic and Clinical Basis of Infectious Diseases, Third Edition. Youmans et al., eds. W.B. Saunders Company: Philadelphia, 1985:618-29, 738-9.

Yudina et al., Synthesis of five nona-β-(1→6)-d-glucosamines with various patterns of N-acetylation corresponding to the fragments of exopolysaccharide of *Staphylococcus aureus*. Carbohydr Res. May 15, 2011;346(7):905-13. Epub Feb. 23, 2011.

Burgeot et al., Immunopotentiation of *Staphylococcus aureus* type 5 capsular polysaccharide co-entrapped in liposomes with alpha-toxin. Vaccine. Feb. 28, 2001;19(15-16):2092-9.

O'Brien et al., Production of antibodies to *Staphylococcus aureus* serotypes 5, 8, and 336 using poly(DL-lactide-co-glycolide) microspheres. J Dairy Sci. Aug. 2000;83(8):1758-66.

Pavliak, Carb 40-*Staphylococcus aureus* capsular polysaccharide—MSCRAMM protein conjugate vaccines. The 232nd ACS National Meeting, San Francisco, CA. Sep. 10-14, 2006:40.

Thoma et al., Novel glycodendrimers self-assemble to nanoparticles which function as polyvalent ligands in vitro and in vivo. Angew Chem Int Ed Engl. Sep. 2, 2002;41(17):3195-8.

Hermanson, Bioconjugate Techniques. Academic Press. 1996:34, 187-248.

Sundgreen et al., Varied presentation of the Thomsen-Friedenreich disaccharide tumor-associated carbohydrate antigen on gold nanoparticles. Carbohydr Res. Jul. 21, 2008;343(10-11):1594-604. doi: 10.1016/j.carres.2008.05.003. Epub May 8, 2008.

METHODS AND COMPOSITIONS RELATING TO SYNTHETIC β-1,6 GLUCOSAMINE OLIGOSACCHARIDES

RELATED APPLICATIONS

This application is a national stage filing under 35 U.S.C. §371 of International Application No. PCT/US2009/004206 filed Jul. 21, 2009 which was published under PCT Article 21(2) in English, and which claims priority under 35 U.S.C. §119 (e) to U.S. provisional applications 61/135,493 and 61/208,155, filed on Jul. 21, 2008 and Feb. 20, 2009, respectively, the entire contents of all of which are incorporated by reference herein.

GOVERNMENT SUPPORT

The present invention was supported in part by a grant from the United States National Institutes of Health RO1AI046706. The U.S. Government has rights in the invention.

FIELD OF THE INVENTION

The invention relates to compositions and methods relating to synthetic oligo-β-(1→6)-2-amino-2-deoxy-D-glucopyranosides which are referred to herein interchangeably as oligo-β-(1→6)-D-glucosamines or oligoglucosamines.

BACKGROUND OF THE INVENTION

*Staphylococci* are gram-positive bacteria which normally inhabit and colonize the skin and mucus membranes of humans. If the skin or mucus membrane becomes damaged during surgery or other trauma, the *Staphylococci* may gain access to internal tissues causing infection to develop. If the *Staphylococci* proliferate locally or enter the lymphatic or blood system, serious infectious complications such as those associated with *Staphylococcal* bacteremia may result. These complications include septic shock, endocarditis, arthritis, osteomyelitis, pneumonia, and abscesses in various organs.

*Staphylococci* include both coagulase-positive organisms that produce a free coagulase and coagulase-negative organisms that do not produce this free coagulase. *Staphylococcus aureus* is the most common coagulase-positive form of *Staphylococci*. *S. aureus* generally causes infection at a local site, either extravascular or intravascular, which ultimately may result in bacteremia. *S. aureus* is also a leading cause of acute osteomyelitis, and causes *Staphylococcal* pneumonia infections. Additionally, *S. aureus* is responsible for approximately 1-9% of the cases of bacterial meningitis and 10-15% of brain abscesses.

There are at least thirty-one known species of coagulase-negative *Staphylococci*, including *S. epidermidis, S. saprophyticus, S. hominis, S. warneri, S. haemolyticus, S. saprophiticus, S. cohnii, S. xylosus, S. simulans,* and *S. capitis. S. epidermidis* is the most frequent infection-causing agent associated with intravenous access devices, and the most frequent isolate in primary nosocomial bacteremias. *S. epidermidis* is also associated with prosthetic valve endocarditis.

*Staphylococcus* is also a common source of bacterial infection in animals. For instance, *Staphylococcal* mastitis is a common problem in ruminants such as cattle, sheep, and goats. The disease is generally treated with antibiotics to reduce the infection but the treatment is a costly procedure and still results in a loss of milk production. The most effective vaccines identified to date are live, intact *S. aureus* vaccines administered subcutaneously. The administration of live vaccines, however, is associated with the risk of infection. For that reason, many researchers have attempted to produce killed *S. aureus* vaccines and/or to isolate capsular polysaccharides or cell wall components which will induce immunity to *S. aureus*.

Carrier compounds are sometimes used in vaccines in order to enhance the immune response to the antigen. For example, the carrier in some vaccines is useful for stimulating T cell help in response to the antigenic moiety. Antigenic moieties that are naturally occurring or fragments of naturally occurring substances are sometime less amenable and less facilely manipulated and/or conjugated to other moieties such as for example carrier compounds, and this can reduce the therapeutic impact of such vaccines.

SUMMARY OF THE INVENTION

The invention provides novel methods and compounds for generating antigenic compositions such as but not limited to vaccines. In particular, the invention provides novel methods for modifying oligosaccharide antigens. These methods involve the controlled synthesis of oligosaccharide (a) comprised of a predetermined order of monosaccharide monomers and (b) conjugated to a carrier compound. The resulting conjugates are better able to stimulate (whether by induction or enhancement) an immune response to the microbial polysaccharide antigen of interest. As described herein, such immune responses are useful in the treatment and/or prevention of various infections including but not limited to *Staphylococcal* infections.

Various aspects of the invention relate to particular linkers (or linking agents or spacers or linking reagents, as the terms are used interchangeably herein), and their use in synthesizing conjugates. Of particular interest are conjugates of oligosaccharides and various carrier compounds. These oligosaccharides include oligo-β-(1→6)-D-glucosamine (linked glucosamine, as referred to herein) which is a comprised of glucosamine monomers attached to each other by a β-(1→6) linkage. One or more of the various monomers that make up the linked glucosamine may be N-acetylated. Thus, the monomers may be D-glucosamine or N-acetyl-D-glucosamine monomers, and the linked glucosamine may comprise a defined order of one or both types of these monomers (or monosaccharides, as the terms are used interchangeably herein). The oligoglucosamines of the invention also comprise spacers having thiol containing groups on their "reducing" ends. The spacer is used to link the oligoglucosamines to carriers. The carriers may be comprised of amino acids (such as peptides or proteins) although they are not so limited.

Thus, in one aspect, the invention provides a compound of Formula I

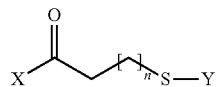

Formula I where X is any atom or group, Y is a sulfur blocking group, and n is greater than 1. In one embodiment, Y is an acyl group. In another embodiment, Y is an acetyl group, and the compound has the structure of Formula II Formula II

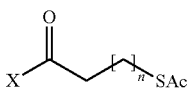

wherein Ac is an acetyl group.

In still another embodiment, the compound is an activated ester of Formula I. In another embodiment, the compound is a cyano, azido or haloid derivative an activated ester of Formula I. In another embodiment, the compound has the structure of Formula III Formula III

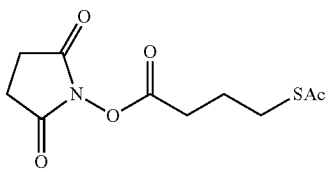

wherein Ac is an acetyl group, and the compound is referred to as N-hydroxysuccinimidyl 4-acetylsulfanyl butyrate. In another embodiment, the compound has the structure of Formula IV Formula IV

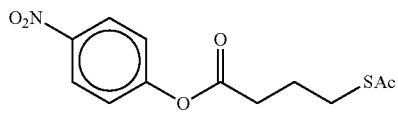

wherein Ac is an acetyl group and the compound is referred to as N-nitrophenyl 4-acetylsulfanyl butyrate.

In another aspect, the invention provides a method for synthesizing N-hydroxysuccinimidyl 4-acetylsulfanyl butyrate (Formula III) comprising reacting 4-acetylsulfanyl-butyric acid (Formula V)

Formula V

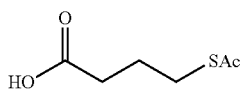

with N-hydroxysuccinimidyl trifluoroacetate (CF$_3$COOSu) to yield N-hydroxysuccinimidyl 4-acetylsulfanyl butyrate (Formula III).

In another aspect, the invention provides a method for synthesizing N-nitrophenyl 4-acetylsulfanyl butyrate (IV) comprising reacting 4-acetylsulfanylbutyric acid (Formula V)

Formula V

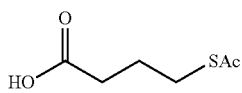

with N-nitrophenyl trifluoroacetate (CF$_3$COOpNp) to yield N-nitrophenyl 4-acetylsulfanyl butyrate (Formula IV).

In another aspect, the invention provides a method for synthesizing an oligosaccharide conjugated to a carrier comprising reacting an oligosaccharide (a) first with a compound having a structure of Formula Va or Vb Formula Va

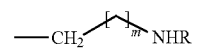

Formula Vb

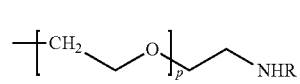

wherein m is a number selected from 1 to 10, p is a number selected from 1 to 20, and R is H or a alkyl group, (b) second with a compound of Formula I, II, III or IV, and (c) third with a carrier, wherein the oligosaccharide is β-1-6 linked glucosamine.

In yet another aspect, the invention provides a composition comprising an oligosaccharide bearing an O-linked linker, wherein the linker comprises Formula VI

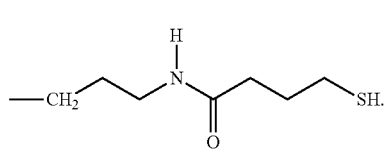

In one embodiment, the oligosaccharide is β-1-6 linked glucosamine. In another embodiment, the oligosaccharide is 2-20 monomers in length. In another embodiment, the oligonucleotide is 5-11 monomers in length. In still another embodiment, the oligosaccharide is 7, 9 or 11 monomers in length.

In one embodiment, the oligosaccharide is 0% acetylated or 100% acetylated. In another embodiment, the oligosaccharide is 0-40% acetylated.

In still another aspect, the invention provides a composition comprising an oligosaccharide-carrier conjugate comprising an oligosaccharide conjugated to a carrier through a linker that is Formula VIIIa

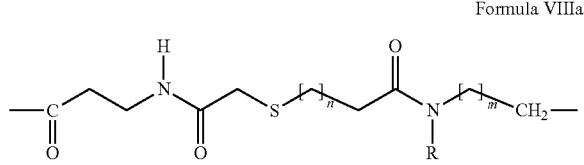

Formula VIIIb

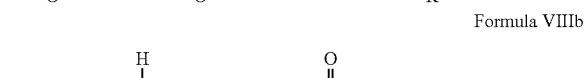

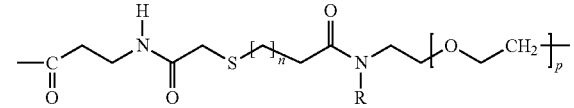

wherein the linker is O-linked to the oligosaccharide and N-linked to the carrier.

In still another aspect, the invention provides a method for synthesizing an oligosaccharide-carrier conjugate comprising reacting an oligosaccharide conjugated to a linker of Formula IXa or IXb Formula IXa

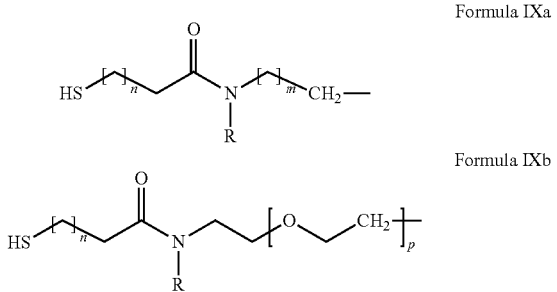

Formula IXb with a carrier having modified amino group following reaction with a compound of Formula Formula X

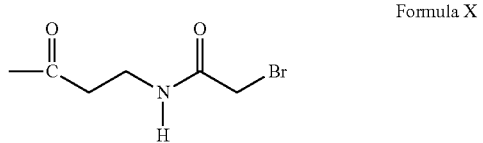

to yield an oligosaccharide conjugated to a carrier compound through a linker having a structure of Formula VIIIa or VIIIb.

In one embodiment, the carrier is a peptide. In another embodiment, the carrier is a protein. An example of a carrier is tetanus toxoid.

In one embodiment, the oligosaccharide is β-1-6 linked glucosamine.

In one embodiment, the composition has a oligosaccharide to carrier ratio of 1:1, 2:1, 3:1, 4:1, 5:1, 6:1, 7:1, 8:1, 9:1, 10:1, 20:1, 30:1, 40:1, 50:1, 60:1, 70:1, 80:1, 90:1 or 100:1.

In some embodiments, the oligosaccharide is 2-20 monomers in length, 5-11 monomers in length, or 5, 7, 9 or 11 monomers in length.

In one embodiment, the oligosaccharide is 100% acetylated. In another embodiment, the oligosaccharide is 0% acetylated. In still another embodiment, the oligosaccharide is 0-40% acetylated.

In some embodiments, the composition further comprises a pharmaceutically acceptable carrier, an adjuvant, and/or an anti-bacterial agent.

In another aspect, the invention provides a method for stimulating an immune response in a subject comprising administering to a subject in need thereof an oligosaccharide-carrier conjugate as described above or an oligosaccharide-carrier conjugate synthesized by a method described above in an amount effective to stimulate an immune response in the subject.

In one embodiment, the subject is a human. In another embodiment, the subject is non-human.

In another embodiment, the method further comprises isolating antibodies or antibody-forming cells from the subject.

In another embodiment, the method further comprises administering an adjuvant to the subject. In another embodiment, the method further comprises administering an anti-bacterial agent to the subject.

In still another aspect, the invention provides a method for treating or preventing a infection in a subject comprising administering to a subject having or at risk of developing an infection an effective amount for inducing an immune response of an oligosaccharide-carrier conjugate as described above or an oligosaccharide-carrier conjugate synthesized by a method as described above, wherein the infection is caused by a bacterial species that makes or is capable of making PNAG.

In one embodiment, the infection is a *Staphylococcus* infection. In a related embodiment, the *Staphylococcus* infection is *Staphylococcus aureus* infection. In another related embodiment, the *Staphylococcus* infection is *Staphylococcus epidermidis*. In one embodiment, the subject is at risk of exposure to *Staphylococcus*. In another embodiment, the subject has been exposed to *Staphylococcus*.

In other embodiments, the infection is an *E. coli* infection, a *Y. pestis* infection, a *Y. entercolitica* infection, a *Y. pseudotuberculosis* infection, an *Aggregatibacter actinomycetemcomitans* infection, an *Actinobacillus pleuropneumoniae* infection, a *Bordetella pertussis* infection, a *B. parapertussis* infection, a *B. bronchiseptica* infection, an *Acinetobacter* infection, a *Burkholderia* infection such as *Burkholderia cenocepacia*, a *Stenatrophomonas maltophilia* infection, a *Shigella* infection, or a *Klebsiella* infection such as *Klebsiella pneumoniae*.

In some embodiments, the oligosaccharide-carrier conjugate is administered with an adjuvant and/or an anti-bacterial agent.

In still another aspect, the invention provides a method for producing antibodies comprising administering to a subject an effective amount, for producing antibodies specific for native PNAG, of an oligosaccharide-carrier conjugate as described above or an oligosaccharide-carrier conjugate synthesized by a method as described above, and isolating antibodies from the subject.

In another aspect, the invention provides a method for producing monoclonal antibodies comprising administering to a subject an effective amount, for producing antibodies specific for native PNAG, of an oligosaccharide-carrier conjugate as described above or an oligosaccharide-carrier conjugate synthesized by a method as described above, harvesting antibody-producing cells from the subject, fusing the antibody-producing cells from the subject to myeloma cells, and harvesting antibody produced from a fusion subclone.

In one embodiment, the antibodies are polyclonal antibodies. In one embodiment, the subject is a rabbit. In another embodiment, the subject is a human.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE FIGURES

FIG. 7, SF8300 (NT, USA300)) by rabbit antisera (bleed 1) to fully acetylated or non-acetylated 9-mer oligoglucosamine (9GlcNH$_2$) conjugated to TT (9GlcNH$_2$-TT). For comparison, killing of the same bacteria by an antiserum raised to a conjugate vaccine consisting of the dPNAG molecule of ~100 kDa conjugated to tetanus toxoid (TT) and further labeled (051).

FIG. 10, LAC (non-typable (NT), USA300)); FIG. 11, SF8300 (NT, USA300)); FIG. 12, Newman (CP5); FIG. 13, PS80; FIG. 14, Reynolds (CP5); FIG. 15, Reynolds (non-typable); FIG. 16, Reynolds (CP8)) by a rabbit antiserum (labeled "bleed 2") to fully acetylated or non-acetylated 9-mer oligoglucosamine conjugated to TT. For comparison, killing of the same bacteria by an antiserum raised to a conjugate vaccine consisting of the dPNAG molecule of ~100 kDa conjugated to tetanus toxoid (TT) and further labeled (051).

DETAILED DESCRIPTION OF THE INVENTION

Figure 1A:
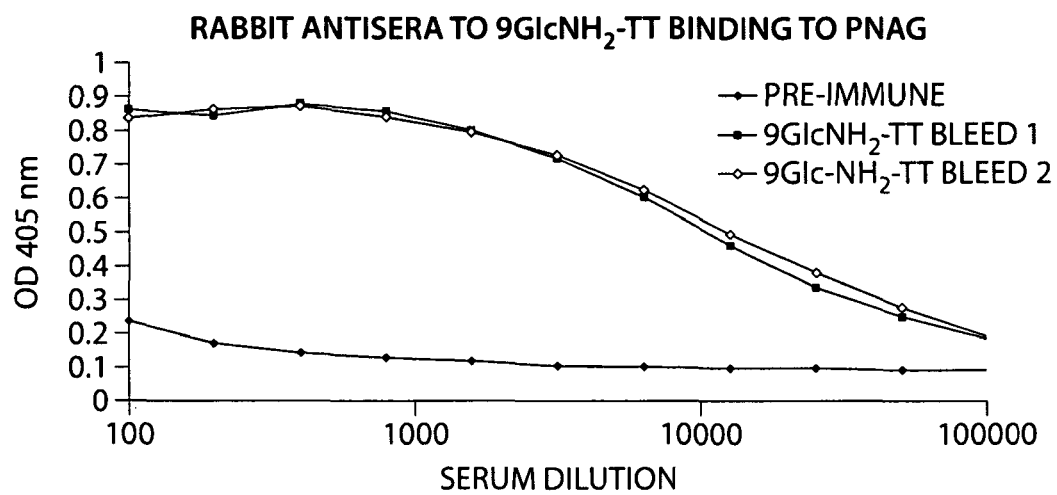
FIGS. 1A and B are graphs showing binding of antisera raised to non-acetylated nona-glucosamine (9GlcNH$_2$) to PNAG (A) or dPNAG (B) from *S. aureus*.
Figure 1B:
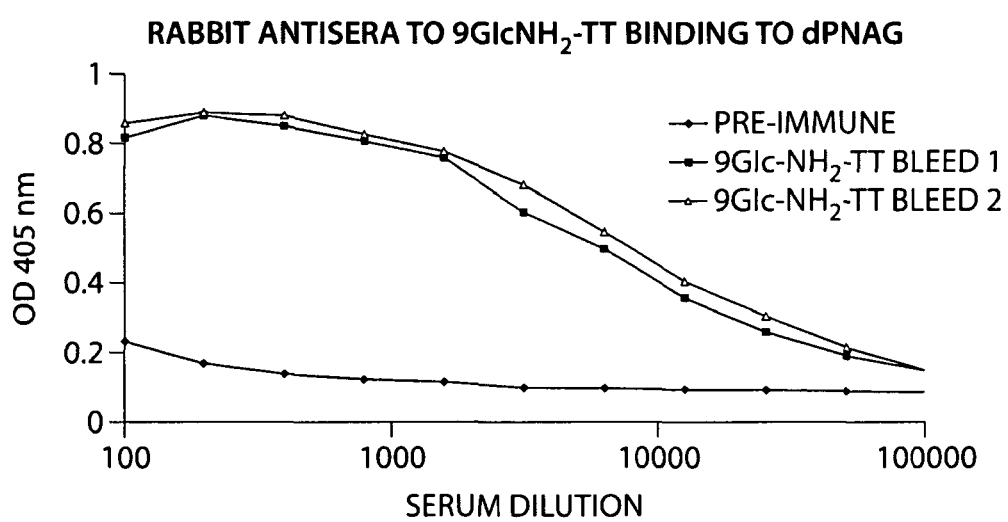

The invention relates broadly to the synthesis and use of oligosaccharide conjugates. The invention provides de novo synthesis methods and the compositions used therein to generate novel compositions. These synthetic routes facilitate modification of the oligosaccharide or polysaccharide that would not otherwise be possible using naturally occurring polysaccharide antigens.

The invention provides inter alia methods for the preparation of oligo-β-(1→6)-D-glucosamine oligosaccharides or polysaccharides having a defined order of monomers, methods for the conjugation of such oligosaccharides or polysaccharides to linkers for subsequent conjugation to carrier compounds, methods for the preparation of the oligosaccharide-carrier conjugates or polysaccharide-carrier conjugates, and compositions of these various compounds. The invention further relates to various novel linkers that are unexpectedly more useful than previously known linkers in these preparation methods. The resultant oligosaccharide-carrier conjugates are useful for stimulating an immune response in vivo in human and non-human subjects, including generation of antibodies to the oligosaccharide themselves and the corresponding naturally occurring PNAG and dPNAG antigens.

PNAG and dPNAG antigens are described in greater detail in published PCT application WO 2004/043405. Briefly, PNAG refers to poly N-acetyl glucosamine which is a surface polysaccharide made by various bacterial species including but not limited to Staphylococci, such as S. aureus and S. epidermis. PNAG exists naturally in both highly and poorly acetylated forms. A "highly acetylated" form of PNAG is a PNAG having greater than 50% acetate substitutions. Poorly acetylated forms of PNAG (referred to herein as dPNAG) may have 0-40% acetylation. (See Formula VII where $R^1$ represents the location of the acetyl group, if present.) Native PNAG is a mixture of PNAG forms with varying degrees of acetylation. Native PNAG may include dPNAG in a mixture with more highly acetylated forms of PNAG. PNAG or dPNAG may be comprised of hundreds or thousands or more glucosamine units (or monomers).

The oligosaccharides of the invention are intended to mimic regions of PNAG or dPNAG. Thus, when used in vivo the oligosaccharide-carrier conjugates induce immune responses directed to regions of the oligosaccharide that are similar or identical to PNAG and/or dPNAG and therefore such immune responses are useful in targeting bacterial species that make or are capable of making PNAG and/or dPNAG.

In some aspects of the invention, the oligosaccharides are comprised of only D-glucosamine, or only N-acetyl-D-glucosamine units, or a predetermined ratio and order of both types of these monomers. The ratio and order is intended to mimic in some embodiments the ratios and orders found in native PNAG. The oligosaccharides are manipulated according to the invention to comprise a spacer (or a linker, as the terms are used interchangeably herein) having a thiol group at its terminus (e.g., its reducing end).

The preparation of oligosaccharides comprising amine groups, such as linked glucosamine oligosaccharides (or oligoglucosamines, as the terms are used interchangeably herein) suitable for conjugation to one or more carriers has proved challenging in the art. This is partly because the stereo-specific synthesis of linked glucosamine requires the use of participating but temporary acyl N-protecting groups (so-called "participating" groups) in the glycosyl donors in order to form the necessary β-glycoside bond between the monomers. N-phthaloyl, N-trichloroethoxycarbonyl and some other moieties are suitable as participating groups. Certain other participating groups however are less suitable including the N-acetyl participating groups that are present in some of the oligosaccharides contemplated by the invention. As an example, N-acetylated glycosyl donors are of low reactivity and give only moderate yields of glycosylation products. In addition, the presence of N-acetyl groups in glycosyl donor complicates the glycosylation reaction due to oxazoline intermediate formation, migration of N-acetyl groups, and other undesirable chemical reactions.

With regards to linked glucosamines, their structure and more particularly the number of amino groups they contain necessitates the introduction of the linker before total liberation of amino groups. Removal of the above-mentioned temporary N-protecting group to prepare free oligosaccharide is carried out under basic conditions. The most effective reagent for removal of an N-phthaloyl participating group is hydrazine hydrate in boiling ethanol. This reagent also effectively removes O-acyl protecting groups including acetyl and benzoyl groups which may be contained in the oligosaccharide of interest.

Commercially available linkers that have been used for the attachment of amino-containing ligands to proteins are pentafluorophenyl S-acetylthioglycolate (chemical structure 8 shown in the Examples) and N-hydroxysuccinimidyl 3-acetylsulfanyl-propionate (chemical structure 12 shown in the Examples). These linking reagents can be used to introduce a thiol moiety into a oligosaccharide; however, as described in greater detail in the Examples, both were unstable under the conditions of removal of phthaloyl groups. Example 5 shows that a linker based on thioglycolic acid undergoes oxidative rearrangement, and Example 6 shows that a derivative of 3-mercaptopropionic acid gives a complex mixture of side products. Both transformations result in loss of the necessary thiol function.

The invention therefore is based in part on the discovery and use of a class of linkers that is effective and better than previously known linkers for conjugating oligosaccharides (including amine containing versions thereof) to a carrier such as a protein. This class of linkers is defined as derivatives of ω-acetylsulfanyl carbonic acid of Formula I (where n>1).

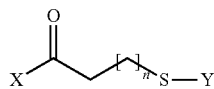

Formula I

This class of linkers provides effective N-acylation during attachment to an oligosaccharide. The linker may be an activated ester of Formula I or its cyano, azido, or haloid derivative. It may be another derivative of Formula I provided such derivative is active as an acylating agent and thus suitable for attachment to oligosaccharides of the present invention. Y represents a temporary blocking group of sulfur atoms, which are known in the art and which include acyl and acetyl groups. Removal of the Y group liberates an SH group which is needed for attachment of the oligosaccharide to the carrier. X represents any leaving group that provides the necessary acylating ability to the compound of Formula I.

It is to be understood that any of the linker classes provided by the invention can be used to conjugate oligosaccharides to carrier compounds.

As an example, one linker class may comprise the structure of Formula II (where n>1):

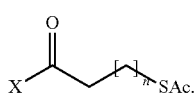

Formula II

As another example, another linker class may comprise N-hydroxysuccinimidyl derivatives. An example of such a linker, as described in Examples 1 and 3, is N-hydroxysuccinimidyl 4-acetylsulfanyl butyrate (compound 2 on Scheme 1, Examples 1 and 3). This linker has the structure of Formula III as follows:

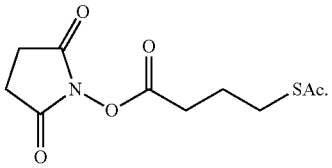

Formula III

ⓘ indicates text missing or illegible when filed

This linker is stable under conditions of total deprotection of carbohydrates such as oligosaccharides and polysaccharides.

Another example of an activated ester is N-nitrophenyl 4-acetylsulfanyl butyrate (compound 3, Examples 2 and 3). This compound has the structure of Formula IV as follows:

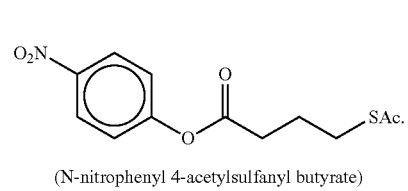

Formula IV (N-nitrophenyl 4-acetylsulfanyl butyrate)

The invention provides a method for synthesizing N-hydroxysuccinimidyl 4-acetylsulfanyl butyrate (Formula III). This method involves reacting 4-acetylsulfanylbutyric acid (Formula V)

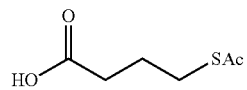

Formula V with N-hydroxysuccinimidyl trifluoroacetate ($CF_3COOSu$) to yield N-hydroxysuccinimidyl 4-acetylsulfanyl butyrate (Formula III).

The invention further provides a method for synthesizing N-nitrophenyl 4-acetylsulfanyl butyrate (Formula IV). This method involves reacting 4-acetylsulfanylbutyric acid (Formula V)

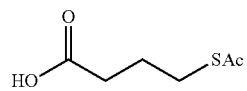

Formula V with N-nitrophenyl trifluoroacetate ($CF_3COOpNp$) to yield N-nitrophenyl 4-acetylsulfanyl butyrate (Formula IV).

These synthesis methods are described in greater detail in the Examples.

The invention further provides compositions comprising an oligosaccharide comprising a linker conjugated to the O1-atom of the glucosamine unit at the "reducing end" of the oligosaccharide. This O1-conjugated linker is used to attach an SH-containing linker via the reaction with the compound of Formula I. The O1-conjugated linker have the structure of Formula Va (below) having an aminoalkyl group and where m may vary from 1 to 10 and R may be H or a simple alkyl group (e.g., a methyl or an ethyl group). Alternatively, an O1-conjugated linker may have the structure of Formula Vb (below) where p may vary from 1 to 20 and R is the same as in Formula Va.

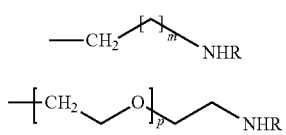

Formula Va

Formula Vb

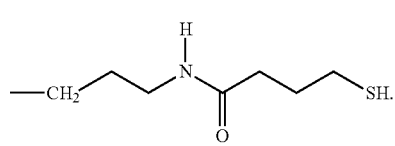

The oligosaccharides conjugates of the present invention therefore may be synthesized by coupling the compounds of Formula Va or Vb with the compound of Formula I. The transformation and subsequent removal of the temporary S-blocking group (Example 8) or reduction of the corresponding intermediate disulfide (Example 7) results in the generation of a final linking group used in the conjugation of the oligosaccharides with a carrier compound. Such final linking groups are described in Examples 7 and 8 have the structure of Formula VI Formula VI

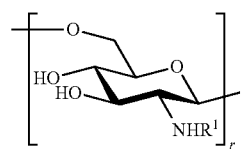

The oligosaccharide may comprise 2, 3, 4, 5, 6, 7, 8, 9, 10, 11, 12, 13, 14, 15, 16, 17, 18, 19, 20, 30, 40, 50, 60, 70, 80, 90 or 100 monosaccharide monomers. In some important embodiments, the oligosaccharide comprises 5 or more monomers including 5, 7, 9 or 11 monomers. In some embodiments, the oligosaccharide comprises 2-20 monomers, or 3-20 monomers, or 4-20 monomers, or 5-20 monomers.

In some important embodiments, the monomer is glucosamine and the oligosaccharide is a linked glucosamine. The structure of a glucosamine monomer (as present in a linked glucosamine) is as follows:

Formula VII where $R^1$ is H in the case of glucosamine units with a "free" amino group, or $R^1$ is an acetyl group ($COCH_3$) in the case of N-acetylated glucosamine units. These units are connected through β-(1→6)-linkages. Any number of glucosamine units may be linked, including 2, 3, 4, 5, 6, 7, 8, 9, 10, 50, or more units up to 100 units (whether substituted with acetyl groups or unsubstituted).

The degree of N-acetylation in the compounds of Formula VII may vary. It may range from 0-50% N-acetylation (i.e., 0-50% of $R^1$ are acetyl groups), including 0-40% N-acetylation. In some embodiments, the β-(1→6) linked glucosamine is less than 50%, less than 40%, less than 30%, less then 20%, less then 10%, or less than 5% N-acetylated. In some important embodiments, the level of N-acetylation and the position of acetyl groups within an oligosaccharide are known by virtue of the synthesis method. That is, the oligosaccharide may be synthesized from the ordered arrangement of glucosamine units having or lacking N-acetyl groups. The Examples provide methods for producing oligosaccharides having defined and ordered acetyl substitutions. In addition, reference can be made to Gening et al. Carbohydrate Research 2007 342:567-575, Gening et al. Russian J Bioorganic Chem 2006 32(4):389-399, Yang and Du Carbohydrate Research 2003 338:495-502, Yang et al. Carbohydrate Research 2003 338:1313-1318, and Fridman et al. Organic Letters 2002 4(2):281-283.

The invention still further provides a composition comprising an oligosaccharide-carrier conjugate comprising an oligosaccharide conjugated to a carrier compound through a linker of Formula VIIIa or VIIIb.

Formula VIIIa

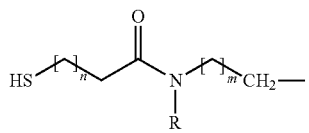

Formula VIIIb

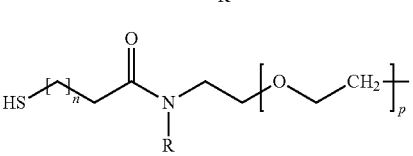

wherein the linker is O-linked to the oligosaccharide and N-linked to the carrier compound.

The invention further provides a method for synthesizing an oligosaccharide-carrier conjugate by reacting oligosaccharide conjugates comprising SH-terminated linkers such as those having structures of Formula IXa or IXb Formula IXa

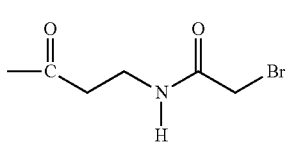

(in the case of compounds from Examples 7 and 8) with a carrier compound in which terminal amino groups are modified by attachment of a compound of Formula X Formula X to yield an oligosaccharide conjugated to a carrier compound through a linker having a structure of Formula VIIIa or VIIIb.

In some embodiments, a linker of Formula VIIIa or VIIIb is linked through its terminal $CH_2$-group to the O1-atom of glucosamine unit at the "reducing end" of the oligosaccharide. Such a linkage is considered an O-linkage, and the oligosaccharide is referred to as being O-linked to the linker.

In some embodiments, a linker of Formula VIIIa or VIIIb is linked through the terminal CO group to an amino group in the carrier compound by an amide bond. Such a linkage is considered an N-linkage, and the carrier is referred to as being N-linked to the linker.

Preparation of conjugates of amino-group-containing carrier and oligoglucosamines having an SH-terminated linker, as described above and in Examples 8 and 9, may use the reagent SBAP. The invention however contemplates the use of other reagents suitable for linking amino-group-containing carriers and SH-terminated oligosaccharides (particularly as described by G. Hermanson "Bioconjugate Techniques", $2^{nd}$ Edition, Academic Press, 2008).

Carrier Compound

A "carrier compound" (or carrier, as the terms are used interchangeably herein) as used herein is a compound that is conjugated to the oligosaccharide through the use of a linker of the invention. Typically, the carrier compound is one that enhances the immune response to the oligosaccharide ligand.

Carrier compounds include but are not limited to proteins, peptides, polysaccharides, nucleic acids, or other polymers, lipids, and small oligomeric molecules, particularly the dendrimers. In some embodiments, the carrier compound may be naturally occurring or may be derived from a naturally occurring entity. Proteins include, for example, plasma proteins such as serum albumin, immunoglobulins, apolipoproteins and transferrin; bacterial polypeptides such as tetanus toxoid (TT), TRPLE, β-galactosidase, polypeptides such as herpes gD protein, allergens, diphtheria toxoid, salmonella flagellin, hemophilus pilin, hemophilus 15 kDa, 28-30 kDa and 40 kDa membrane proteins, *Escherichia coli* heat label enterotoxin ltb, cholera toxin, and viral proteins including rotavirus VP and respiratory syncytial virus f and g proteins. The carriers useful in the invention include any protein that is safe for administration to mammals and optionally that is an immunologically effective carrier protein. Thus, in some embodiments, the carrier compound may itself be immunogenic. Examples include compounds that have been used in or as vaccines against a bacterial species such as but not limited to those listed herein.

Carrier compounds that are useful particularly for immunization include proteins such as keyhole limpet hemocyanin, serum albumin, bovine thyroglobulin, or soy bean trypsin inhibitor. Any other compound that is immunogenic in the species of animal to be immunized can similarly be used.

As shown in the Examples, the oligosaccharide to carrier ratio in the oligosaccharide-carrier conjugates of the invention may vary. For example, an oligosaccharide-carrier conjugate may have an oligosaccharide to carrier ratio of 1:1, at least 2:1, at least 3:1, at least 4:1, at least 5:1, at least 6:1, at least 7:1, at least 8:1, at least 9:1 or at least 10:1. In still other embodiments, the ratio may be at least 20:1, at least 30:1, at least 40:1, at least 50:1, at least 60:1, at least 70:1, at least 80:1, at least 90:1, or greater, up to for example 100:1 or 700:1 depending on the capacity of carrier compound for attachment of oligosaccharide ligands. As an example, a conjugate that has an oligosaccharide to carrier ratio of at least 3:1 is a conjugate that has at least three oligosaccharide moieties attached to a single carrier compound.

Utility

The compositions of the invention have a number of in vitro and in vivo uses. For example, the compositions of the invention are useful for producing an antibody response, e.g., as a vaccine for active immunization of humans and animals to prevent infection by species of bacteria that make or are capable of making native PNAG, including but not limited to *Staphylococcus*; as a vaccine for immunization of humans or animals to produce anti-dPNAG antibodies that can be administered to other humans or animals to prevent or treat infections by species of bacteria that make or are capable of making native PNAG, including but not limited to *Staphylococcus*; as an antigen to screen for biological agents such as monoclonal antibodies capable of preventing infection by species of bacteria that make or are capable of making native PNAG, including but not limited to *Staphylococcus*, libraries of genes involved in making antibodies, or peptide mimetics; as a diagnostic reagent for infections by species of bacteria that make or are capable of making native PNAG, including but not limited to *Staphylococcus*; and as a diagnostic reagent for determining the immunologic status of humans or animals in regard to their susceptibility to infections by species of bacteria that make or are capable of making native PNAG, including but not limited to *Staphylococcus*.

Treatment and Prevention of Infections

The invention provides a method for treating or preventing infection by species of bacteria that make or are capable of making native PNAG, including but not limited to *Staphylococcus*, in a subject comprising administering to a subject having or at risk of developing such an infection an effective amount for inducing an immune response of an oligosaccharide-carrier conjugate of the invention.

Another aspect of the invention provides a method for evaluating the ability of a conjugates of the invention to protect against infection by species of bacteria that make or are capable of making native PNAG, including but not limited to *Staphylococcus*, in a subject. The method involves administering to the subject an effective amount of the conjugate, wherein the conjugate induces active immunity, exposing the subject to bacterial species that make or are capable of making native PNAG, and testing for the presence of the bacterial species in the subject.

The subject may be one that is subject is at risk of exposure to the bacterial species, or one that has been exposed to the bacterial species. The conjugate may be administered in a composition together with other agents such as but not limited to one or more adjuvants, and/or one or more anti-bacterial agents, etc.

The infection may be a *Staphylococcus* infection. The *Staphylococcus* infection may a *Staphylococcus aureus* infection, a *Staphylococcus epidermidis* infection, but it is not so limited. The infection may be an *E. coli* infection, a *Y. pestis* infection, a *Y. entercolitica* infection, a *Y. pseudotuberculosis* infection, an *Aggregatibacter actinomycetemcomitans* infection, an *Actinobacillus pleuropneumoniae* infection, a *Bordetella pertussis* infection, a *B. parapertussis* infection, a *B. bronchiseptica* infection, an *Acinetobacter* infection including infection by *Acinetibacter* complex organisms, a *Burkholderia* infection including an infection by *Burkholderia* complex organisms, a *Stenatrophomonas maltophilia* infection, a *Shigella* (different species) infection, and a *Klebsiella* (different species) infection.

The antibodies generated according to the invention may also be used to prevent or treat infection by any infectious or pathogenic microbe that makes a molecule that reacts with the antibodies induced by an immune response to the oligosaccharide-carrier conjugate.

An "effective amount for inducing an immune response (e.g., an antibody response)" as used herein is an amount which is sufficient to (i) assist the subject in producing its own immune protection by e.g. inducing the production of antibodies in the subject, inducing the production of memory cells, and possibly a cytotoxic lymphocyte reaction etc. and/or (ii) prevent infection from occurring in a subject which is exposed to an infectious or pathogenic microbe that makes or is capable of making PNAG, including but not limited to *Staphylococcus*.

In some preferred embodiments, the effective amount of a vaccine for stimulating an immune response is an amount of vaccine that is capable of eliciting the production of antibodies that are cross-reactive with at least two species of *Staphylococcus*, e.g., *S. aureus* and *S. epidermidis*.

One of ordinary skill in the art can assess whether an amount is sufficient to induce active immunity by routine methods known in the art. For instance, the ability of a specific conjugate to produce antibody in a mammal can be assessed by screening for antibodies in a mouse or other subject using conjugates or their corresponding oligosaccharides.

Subjects as used herein include human and non-human subjects. Non-human subjects include but are not limited to companion animals such as dogs, cats, ferrets, birds, and the like, agricultural animals such as cows, pigs, goats, sheep, horses, chickens, and the like, zoo animals such as giraffes, lions, tigers, elephants, bears, and the like, laboratory animals such as mice, rats, rabbits, and the like. The subject may be a human over 60 years of age. The subject may be one that is healthy.

The subjects to be treated according to the invention include hospitalized patients who are at risk of developing *Staphylococcal* infection as a result of exposure to the bacteria in the hospital environment. Particular high risk populations for developing infection by *S. aureus* include, for example, renal disease patients on dialysis, and individuals undergoing high risk surgery. High risk populations for developing infection by *S. epidermidis* also include, for example, patients with indwelling medical devices, such as intravenous lines (e.g., central lines), or prostheses (e.g., hip or knee replacement prostheses), because clinical isolates are often highly adherent to plastic surfaces. In some embodiments, the subject is a subject that has received a medical device implant and in other embodiments, the subject is one that has not received a medical device implant but may be scheduled to receive one. Subjects at a high risk of developing infection by *S. epidermidis* further include, for example, pre-term neonates and patients undergoing chemotherapy. Additional subjects to be treated according to the invention include hospitalized patients or individuals in the community who become ill and who are at risk of developing infections with microbes that make or are capable of making PNAG as a result of exposure to the bacteria in the hospital or community environments.

Immune Response Induction and Antibody Generation

The invention further provides methods for stimulating an immune response in a subject comprising administering to a subject in need thereof an oligosaccharide-carrier conjugate of the invention in an amount effective to stimulate an immune response in the subject. The immune response may be an antigen-specific immune response. It may be a cellular and/or a humoral immune response. For example, the immune response may result in the production of antibodies and/or antibody-producing cells.

"Passive immunity" as used herein involves the administration of antibodies to a subject, wherein the antibodies are produced in a different subject (including subjects of the same and different species), such that the antibodies attach to the surface of the bacteria and cause the bacteria to be phagocytosed.

The antibodies generated using the conjugates of the invention may be administered to any subject at risk of developing an infection by a species that makes PNAG or a species that makes another molecule that reacts with the antibodies to induce passive immunity, and in some embodiments may be particularly suited for subjects incapable of inducing active immunity. Since vaccination with the antigen might not be completely effective in high risk immunocompromised subjects, these subjects will benefit from treatment with antibody preparations raised against the oligosaccharide-carrier conjugates of the invention to prevent or treat infections such as those due to *Staphylococcus aureus*. A subject that is incapable of inducing an immune response is an immunocompromised subject (e.g. patient undergoing chemotherapy, AIDS patient, etc.) or a subject that has not yet developed an immune system (e.g. pre-term neonate).

Thus, the invention provides a method for producing antibodies comprising administering to a subject an effective amount for producing antibodies specific for the PNAG molecule expressed by an organism such as *Staphylococcus* using an oligosaccharide-carrier conjugate of the invention, and isolating antibodies from the subject. The antibodies may be polyclonal antibodies. The antibodies may be further modified.

The invention further provides a method for producing monoclonal antibodies comprising administering to a subject an effective amount for producing antibodies specific for the PNAG molecule using an oligosaccharide-carrier conjugate of the invention, harvesting antibody-producing cells from any tissue containing such cells such as spleen or blood from the subject, fusing the antibody-producing cells from the subject to myeloma cells, and harvesting antibody produced from a fusion subclone.

The invention contemplates the generation of a variety of antibodies specific to the oligo-β-(1→6)-D-glucosamines of present invention. These include chimeric antibodies such as humanized antibodies and antibody fragments, as well as intact monoclonal and polyclonal antibodies. A "humanized monoclonal antibody" as used herein is a human monoclonal antibody or functionally active fragment thereof having at least human constant regions and an antigen binding region (such as 1, 2, 3, 4, 5, or 6 CDRs, or 1 or 2 variable regions, or Fab or F(ab)$_2$ fragments) from a species other than a human. Humanized monoclonal antibodies, for example, may be constructed by replacing the non-CDR regions of a non-human mammalian antibody with similar regions of human antibodies while retaining the epitopic specificity of the original antibody. For example, non-human CDRs and optionally some of the framework regions may be covalently joined to human FR and/or Fc/pFc' regions to produce a functional antibody. European Patent Application 0239400, the entire contents of which is hereby incorporated by reference, provides an exemplary teaching of the production and use of humanized monoclonal antibodies in which at least the CDR portion of a murine (or other non-human mammal) antibody is included in the humanized antibody. There are entities in the United States which will synthesize humanized antibodies from specific murine antibody regions commercially, such as Protein Design Labs (Mountain View Calif.), Abgenix, and Medarex.

An intact humanized monoclonal antibody in an isolated form or in a pharmaceutical preparation is particularly suited to some aspects of the invention. Humanized antibodies have particular clinical utility because they will not evoke an immune response in humans against the antibody itself. In one preferred embodiment, a murine CDR is grafted into the framework region of a human antibody to prepare the "humanized antibody." See, e.g., L. Riechmann et al., Nature 332, 323 (1988); M. S. Neuberger et al., Nature 314, 268 (1985) and EPA 0 239 400 (published Sep. 30, 1987).

Human monoclonal antibodies may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51-63 (Marcel Dekker, Inc, New York, 1987), and Boerner et al., *J. Immunol.*, 147: 86-95 (1991).

In addition to the conventional methods for preparing human monoclonal antibodies, such antibodies may also be prepared by immunizing transgenic animals that are capable of producing human antibodies (e.g., Jakobovits et al., *PNAS USA*, 90: 2551 (1993), Jakobovits et al., *Nature*, 362: 255-258 (1993), Bruggermann et al., *Year in Immunol.*, 7:33 (1993) and U.S. Pat. No. 5,569,825 issued to Lonberg).

Human antibodies may also be obtained by recovering antibody-producing lymphocytes from the blood or other tissues of humans. These lymphocytes can be treated to produce cells that grow on their own in the laboratory under appropriate culture conditions. The cell cultures can be screened for production of antibody to the conjugates of the invention and then cloned. Clonal cultures can be used to produce human monoclonal antibodies, or the genetic elements encoding the variable portions of the heavy and light chain of the antibody can be cloned and inserted into nucleic acid vectors for production of antibody of different types.

Antibody fragments are also encompassed by the invention. Well-known functionally active antibody fragments include but are not limited to F(ab')$_2$, Fab, Fv and Fd fragments of antibodies. These fragments which lack the Fc fragment of intact antibody, clear more rapidly from the circulation, and may have less non-specific tissue binding than an intact antibody (Wahl et al., *J. Nucl. Med.* 24:316-325 (1983)). For example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated variable heavy chain single domain, also have been reported (see, for example, Ward et al., *Nature* 341:644-646 (1989), disclosing a method of screening to identify an antibody heavy chain variable region ($V_H$ single domain antibody) with sufficient affinity for its target epitope to bind thereto in isolated form). Methods for making recombinant Fv fragments based on known antibody heavy chain and light chain variable region sequences are known in the art and have been described, e.g., Moore et al., U.S. Pat. No. 4,462,334. Other references describing the use and generation of antibody fragments include e.g., Fab fragments (Tijssen, Practice and Theory of Enzyme Immunoassays (Elsevieer, Amsterdam, 1985)), Fv fragments (Hochman et al., Biochemistry 12: 1130 (1973); Sharon et al., Biochemistry 15: 1591 (1976); Ehrilch et al., U.S. Pat. No. 4,355,023) and portions of antibody molecules (Audilore-Hargreaves, U.S. Pat. No. 4,470,925). Thus, those skilled in the art may construct antibody fragments from various portions of intact antibodies without destroying the specificity of the antibodies.

Compositions and Pharmaceutical Preparations

The compositions of the invention, including for example the oligosaccharide-carrier conjugates of the invention, may be formulated together with a pharmaceutically acceptable vehicle. The term "pharmaceutically-acceptable vehicle" as used herein means one or more compatible solid or liquid filler, diluents or encapsulating substances which are suitable for administration to a human or other animal. In the present invention, the term "vehicle" denotes an organic or inorganic ingredient, natural or synthetic, with which the active ingredient is combined to facilitate the application. The components of the pharmaceutical compositions also are capable of being commingled with the conjugates, and with each other, in a manner such that there is no interaction which would substantially impair the desired pharmaceutical efficiency.

Thus, the composition of present invention may be regarded as a pharmaceutical preparation. It may be used in vivo, but its use is not so limited. When used in vivo, it may be used in human or non-human subjects, whether for therapeutic, prophylactic or research purposes. As an example, the compositions may be used to generate antibodies and/or antibody producing cells in non-human subjects such as mice, rabbits, and other suitable animal hosts.

The invention therefore provides pharmaceutical preparations comprising any of the foregoing oligosaccharide-carrier conjugates, which may be used as vaccines. These preparations may comprise the conjugates in an amount effective to stimulate an immune response, such as an antigen-specific immune response. These preparations may comprise other constituents or components such as but not limited to adjuvants and anti-bacterial agents. Such preparations may routinely contain pharmaceutically acceptable concentrations of salt, buffering agents, preservatives, compatible carriers, adjuvants, and optionally other therapeutic ingredients.

A suitable carrier media for formulating a vaccine includes sodium phosphate-buffered saline (pH 7.4) or 0.125 M aluminum phosphate gel suspended in sodium phosphate-buffered saline at pH 6 and other conventional media. Generally, vaccines contain from about 5 to about 100 μg, and preferably about 10-50 μg of the antigen to elicit effective levels of antibody in warm-blooded mammals.

An adjuvant is any substance which is incorporated into or administered (simultaneously or otherwise) with an antigen, which potentiates the immune response to the antigen in the subject. Adjuvants include but are not limited to aluminum compounds, e.g., gels, aluminum hydroxide and aluminum phosphate, and Freund's complete or incomplete adjuvant (e.g., in which the antigen is incorporated in the aqueous phase of a stabilized water in paraffin oil emulsion). The paraffin oil may be replaced with different types of oils, e.g., squalene or peanut oil. Other materials with adjuvant properties include BCG (attenuated *Mycobacterium tuberculosis*), calcium phosphate, levamisole, isoprinosine, polyanions (e.g., poly A:U), lentinan, pertussis toxin, lipid A, saponins, QS-21 and peptides, e.g. muramyl dipeptide, and immunostimulatory oligonucleotides such as CpG oligonucleotides. Rare earth salts, e.g., lanthanum and cerium, may also be used as adjuvants. The amount of adjuvants depends on the subject and the particular antigen used and can be readily determined by one skilled in the art without undue experimentation.

An anti-bacterial agent is an agent that kills bacteria (e.g., through lysis) or prevents their division. The use of antibiotics in the treatment of bacterial infection is routine. Anti-bacterial agents include penicillin G, penicillin V, ampicillin, amoxicillin, bacampicillin, cyclacillin, epicillin, hetacillin, pivampicillin, methicillin, nafcillin, oxacillin, cloxacillin, dicloxacillin, flucloxacillin, carbenicillin, ticarcillin, avlocillin, mezlocillin, piperacillin, amdinocillin, cephalexin, cephradine, cefadoxil, cefaclor, cefazolin, cefuroxime axetil, cefamandole, cefonicid, cefoxitin, cefotaxime, ceftizoxime, cefmenoxine, ceftriaxone, moxalactam, cefotetan, cefoperazone, ceftazidme, imipenem, clavulanate, timentin, sulbactam, neomycin, erythromycin, metronidazole, chloramphenicol, clindamycin, lincomycin, vancomycin, trimethoprim-sulfamethoxazole, aminoglycosides, quinolones, tetracyclines and rifampin. (See Goodman and Gilman's, Pharmacological Basics of Therapeutics, 8th Ed., 1993, McGraw Hill Inc.)

The conjugates may be attached covalently or non-covalently to other moieties including but not limited to detectable labels such as imaging agents, fluorophores, enzymes, and the like.

Compositions suitable for parenteral administration conveniently comprise a sterile aqueous preparation, which can be isotonic with the blood of the recipient. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables. Carrier formulations suitable for subcutaneous, intramuscular, intraperitoneal, intravenous, etc. administrations may be found in Remington's Pharmaceutical Sciences, Mack Publishing Company, Easton, Pa.

The preparations of the invention are administered in effective amounts. An effective amount, as discussed above, in some instances is that amount that will alone, or together with further doses, induce active or passive immunity depending on the subject. It is believed that doses ranging from 1 nanogram/kilogram to 100 milligrams/kilogram, depending upon the mode of administration, will be effective. The preferred range is believed to be between 500 nanograms and 500 micrograms/kilogram, and most preferably between 1 microgram and 100 micrograms/kilogram. The absolute amount will depend upon a variety of factors including whether the administration is performed on a high risk subject not yet infected with the bacteria or on a subject already having an infection, the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the compositions of the invention are contemplated. Generally immunization schemes involve the administration of a high dose of an antigen followed by subsequent lower doses of antigen after a waiting period of several weeks. Further doses may be administered as well. The dosage schedule for passive immunization would be quite different with more frequent administration if necessary. Any regimen that results in an enhanced immune response to bacterial infection and/or subsequent protection from infection may be used. Desired time intervals for delivery of multiple doses of a particular conjugate can be determined by one of ordinary skill in the art employing no more than routine experimentation.

A variety of administration routes are available. The particular mode selected will depend, of course, upon the particular conjugate selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are parenteral routes. The term "parenteral" includes subcutaneous, intravenous, intramuscular, intraperitoneal, and intrasternal injection, or infusion techniques. Other routes include but are not limited to oral, nasal, dermal, sublingual, and local.

The following Examples are included for purposes of illustration and are not intended to limit the scope of the invention.

EXAMPLES

Aspects of the invention are further illustrated by the following non-limiting Examples. These Examples illustrate inter alia how to make the oligo-β-(1→6)-D-glucosamine oligosaccharides and how to conjugate such oligosaccharides to carriers such as protein carriers. Such conjugates may be used, inter alia, as vaccines.

Example 1

Synthesis of N-hydroxysuccinimidyl 4-acetylsulfanylbutyrate 2

Scheme 1. Synthesis of the linking reagent 2. a: CF$_3$COOSu, pyridine.

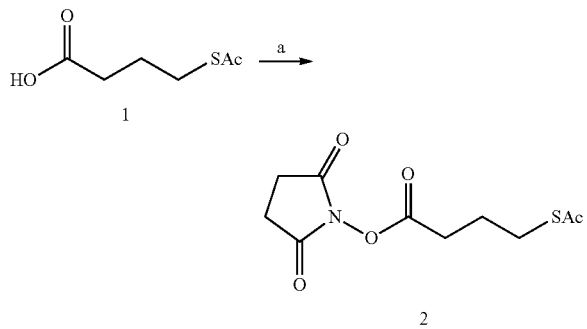

To a solution of the acid 1 (Hogg, J. Heather; Ollmann, Ian R.; Wetterholm, Anders; Andberg, Martina Blomster; Haeggstroem, Jesper; et al.; Chem. Europ. J.; EN; 4; 9; 1998; 1698-1713) (237 mg, 1.46 mmol) and N-hydroxysuccinimidyl trifluoroacetate (431 mg, 2.02 mmol) in dichloromethane (4 mL) was added pyridine (355 µL, 4.4 mmol) and the resulting solution was stirred at room temperature for 2 h. The mixture was diluted with dichloromethane (50 mL), and washed with ice-cold 1 M HCl and water, and concentrated. Silica gel column chromatography (toluene-ethyl acetate 9:1) of the residue gave the active ester 2 (359 mg, 95%) as colorless syrup. $^1$H NMR data (300 MHz, CDCl$_3$), δ 2.00 (m, 2H, (β-CH$_2$), 2.33 (s, 3H, CH$_3$COS), 2.68 (t, 2H, J 7.4 Hz, γ-CH$_2$), 2.81 (s, 4H, 2 CH$_2$ of succinimide), 2.96 (t, 2H, J 7.1 Hz, α-CH$_2$). $^{13}$C NMR data (62.9 MHZ, CDCl$_3$): δ 24.7 (β-CH$_2$), 25.6 (CH$_2$ of succinimide), 27.9 (γ-CH$_2$), 29.7 (α-CH$_2$), 30.7 (CH$_3$COS), 168.0 (CO—ON), 169.2 (CO of succinimide), 195.4 (CH$_3$COS).

Example 2

Synthesis of 4-nitrophenyl 4-acetylsulfanylbutyrate 3

Scheme 2. Synthesis of the linking reagent 3. a: CF₃COOpNp, Et₃N.

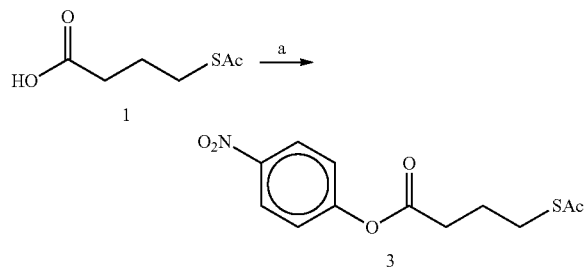

To a solution of the acid 1 (233 mg, 1.44 mmol) (Hogg, J. Heather; Ollmann, Ian R.; Wetterholm, Anders; Andberg, Martina Blomster; Haeggstroem, Jesper; et al.; *Chem. Europ. J.*; EN; 4; 9; 1998; 1698-1713) and 4-nitrophenyl trifluoroacetate (470 mg, 2 mmol) in dichloromethane was added triethylamine (400 μL, 2.88 mmol) and the solution was stirred for 2 h at room temperature. The mixture was worked-up as described for 2 and the active ester 3 (385 mg, 94%) was isolated by silica gel column chromatography (toluene-ethyl acetate 92:8). $^1$H NMR data (300 MHz, CDCl$_3$), δ 2.03 (m, 2H, β-CH$_2$), 2.36 (s, 3H, CH$_3$COS), 2.68 (t, 2H, J 7.2 Hz, γ-CH$_2$), 3.01 (t, 2H, J 7.1 Hz, α-CH$_2$), 7.28, 8.26 (2d, 4H, aromatics). $^{13}$C NMR data (62.9 MHZ, CDCl$_3$): δ 24.7 (β-CH$_2$), 28.0 (γ-CH$_2$), 30.7 (CH$_3$COS), 32.7 (α-CH$_2$), 122.5, 125.2, 145.3, 155.3 (aromatic C), 170.4 (COO), 195.5 (CH$_3$COS).

Example 3

Synthesis of the Ligands 6 and 7 Using Linking Reagent 2 or 3

Scheme 3. Synthesis of the ligands. a: 1) H$_2$, Pd(OH)$_2$/C, MeOH/THF 2) 2 or 3, Et$_3$N, CH$_2$Cl$_2$; b: N$_2$H$_4$·H$_2$O, EtOH, Δ; c: DTT, NaHCO$_3$, Ac$_2$O, MeOH/H$_2$O.

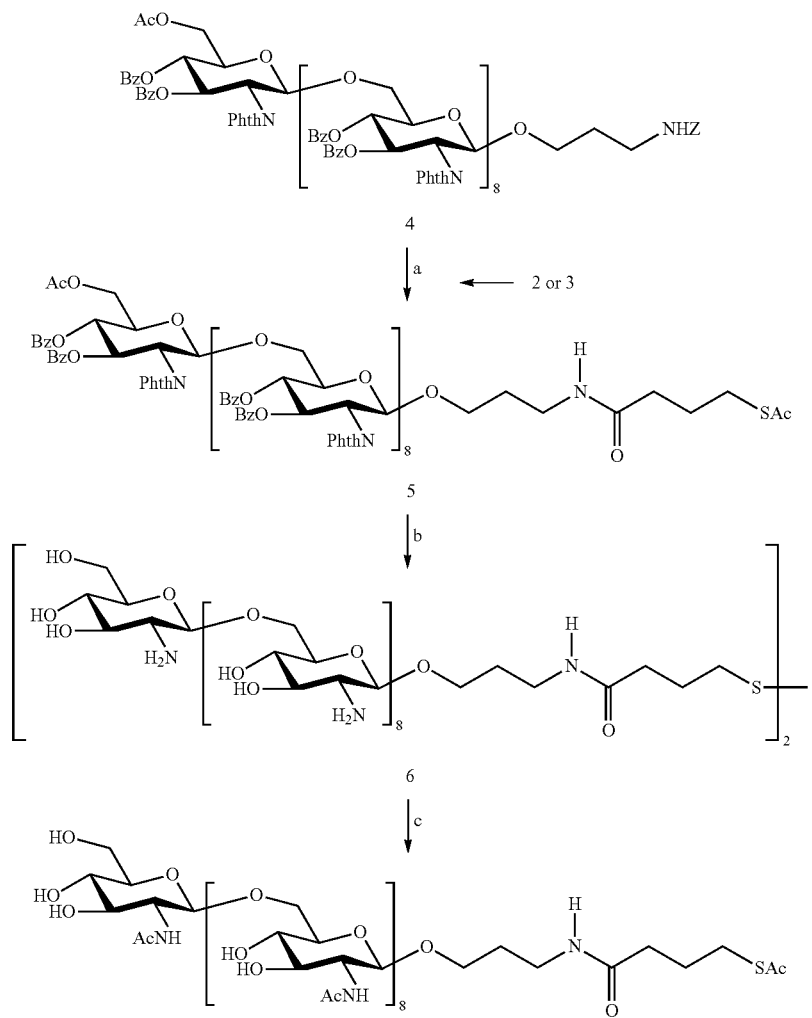

Nonasaccharide 4 (M. L. Gening, Y. E. Tsvetkov, G. B. Pier, N. E. Nifantiev, <<Synthesis of oligo-β(1→6)-glucosamines corresponding to the fragments of the surface polysaccharide of *Staphylococcus aureus*>> *Carbohydr. Res.* 342 (2007), 567-575) (110 mg, 0.023 mmol) was dissolved in a mixture of MeOH (3 ml), THF (6 ml) and 1M HCl (0.2 ml) and Pd(OH)$_2$/C (110 mg) was added. The resultant mixture was stirred under hydrogen atmosphere for 1 h. The catalyst was filtered off and the solvents were evaporated. The residue was dissolved in a mixture of CH$_2$Cl$_2$ (2 ml) and DMF (1 ml) and then linker reagent 2 (12 mg, 0.046 mmol, solution in 1 ml of CH$_2$Cl$_2$) and Et$_3$N (100 μl) were added. After 30 minutes the mixture was diluted with toluene, concentrated and subjected to silica gel column chromatography (toluene/Me$_2$CO, 4:1) to give 5 (98 mg, 98%) as a colorless foam. Introduction of the linker was confirmed by the presence of its characteristic signals in NMR spectra of the protected carbohydrate ligand. $^1$H NMR (500 MHz, CDCl$_3$): δ 1.88 (m, 2H, β-CH$_2$), 2.21 (t, 2H, J 7.2 Hz, γ-CH$_2$), 2.31 (s, 3H, CH$_3$COS), 2.88 (t, 2H, J 7.1 Hz, α-CH$_2$). $^{13}$C NMR data (125 MHZ, CDCl$_3$): δ 25.7 (β-CH$_2$), 28.5 (α-CH$_2$), 30.6 (CH$_3$COS), 35.1 (γ-CH$_2$).

A mixture of the protected nonasaccharide 5 (95 mg, 0.02 mmol), EtOH (5 ml) and N$_2$H$_4$.H$_2$O (0.5 ml) was stirred under reflux for 1 h and then concentrated and subjected to gel permeation chromatography (TSK gel Toyopearl HW 40S, 2.5×40 cm) in 0.1M aqueous AcOH to furnish nonasaccharide 6 (28 mg, 86%). Directly after gel chromatography SH-derivative may be obtained as it was detected by mass-spectrometry, but after storage in solution it converted to corresponding disulfide as it was confirmed by $^{13}$C NMR experiment. $^1$H NMR (500 MHz, D$_2$O): δ 1.95 (m, 2H, (β-CH$_2$), 2.32 (t, 2H, J 7.2 Hz, γ-CH$_2$SH), 2.71 (t, 2H, J 7.1 Hz, α-CH$_2$). $^{13}$C NMR data (125 MHZ, D$_2$O): δ 29.7 (β-CH$_2$), 35.8 (γ-CH$_2$SH), 38.5 (α-CH$_2$), 42.1 (γ-CH$_2$SS). Mass-spectra: calculated for C$_{61}$H$_{114}$N$_{10}$O$_{38}$S 543.234 [M+3H]$^{3+}$, experimental 543.243 [M+3H]$^{3+}$.

Nonasaccharide 6 (15 mg) was dissolved in a mixture of water/MeOH (2 ml, 1:1 v/v) and dithiothreitol (15 mg) and NaHCO$_3$ (20 mg) were added. The resultant mixture was stirred for 5 minutes and then acetic anhydride (100 μl) was added and stirring was continued for 30 minutes before the solvents were evaporated. The product was purified by gel permeation chromatography (TSK gel Toyopearl HW 40S, 2.5×40 cm) in 0.1M aqueous AcOH to give acetylated product 7 (15 mg, 95%) $^1$H NMR (500 MHz, D$_2$O): δ 1.75 (m, 2H, (β-CH$_2$), 2.11 (t, 2H, J 7.2 Hz, γ-CH$_2$), 2.43 (s, 3H, CH$_3$COS), 2.75 (t, 2H, J 7.1 Hz, α-CH$_2$). $^{13}$C NMR data (125 MHZ, D$_2$O): δ 25.7 (β-CH$_2$), 28.5 (α-CH$_2$), 30.6 (CH$_3$COS), 35.1 (γ-CH$_2$). Mass-spectra: calculated for C$_{81}$H$_{134}$N$_{10}$O$_{48}$S 1024.418 [M+2H]$^{2+}$, experimental 1024.427 [M+2H]$^{2+}$ Example 4

Synthesis of the Protected Ligand 5 Using Linking Reagent 3

Nonasaccharide 4 (60 mg, 0.013 mmol) was dissolved in a mixture of MeOH (1.5 ml), THF (3 ml) and 1M HCl (0.1 ml) and Pd(OH)$_2$/C (60 mg) was added. The resultant mixture was stirred under hydrogen atmosphere for 1 h. The catalyst was filtered off and the solvents were evaporated. The residue was dissolved in a mixture of CH$_2$Cl$_2$ (2 ml) and DMF (1 ml) and then linker reagent 3 (20 mg, 0.07 mmol, solution in 1 ml of CH$_2$Cl$_2$) and Et$_3$N (50 μl) were added. After 20 h the mixture was diluted with toluene, concentrated and subjected to silica gel column chromatography (toluene/Me$_2$CO, 4:1) to give 5 (37 mg, 68%) as a colorless foam.

Example 5

Study of Applicability of Linking Reagent 8 for the Preparation of Ligands for Further Conjugation with Protein Scheme 4. Synthesis of the ligands.. a: 1) H$_2$, Pd(OH)$_2$/C, MeOH/THF 2) 8, Et$_3$N, CH$_2$Cl$_2$; b: N$_2$H$_4$•H$_2$O, EtOH, Δ.

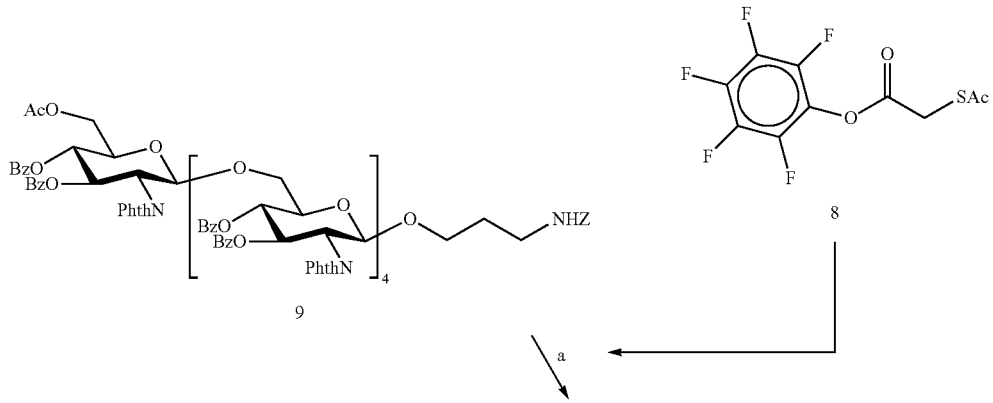

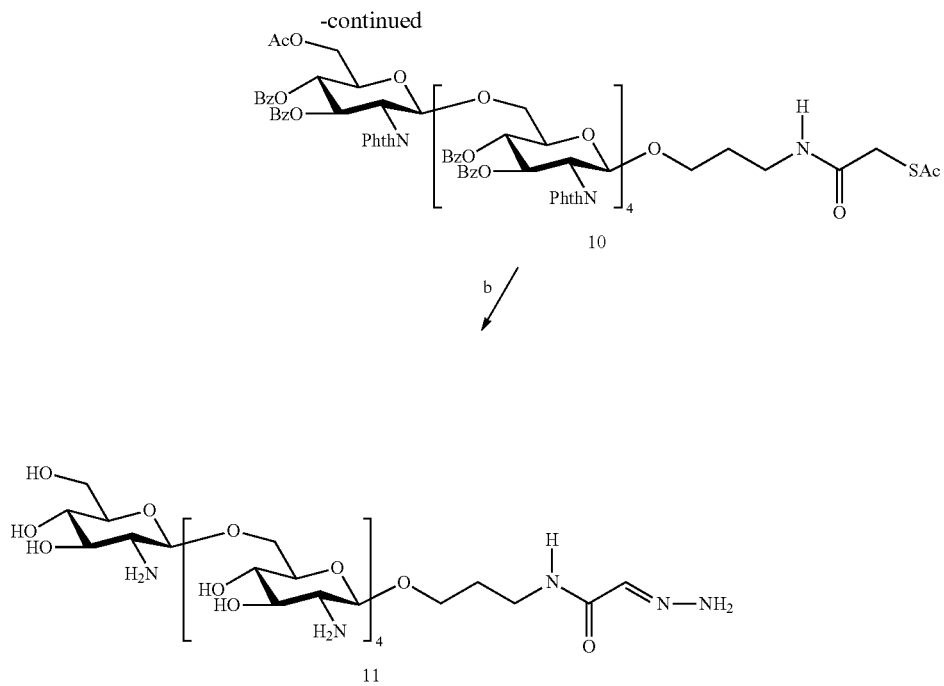

Pentasaccharide 9 (150 mg, 0.026 mmol) (M. L. Gening, Y. E. Tsvetkov, G. B. Pier, N. E. Nifantiev, <<Synthesis of oligo-β(1→6)-glucosamines corresponding to the fragments of the surface polysaccharide of *Staphylococcus aureus*>> *Carbohydr. Res.* 342 (2007), 567-575) was dissolved in a mixture of MeOH (1.5 ml), THF (3 ml) and 1M HCl (0.1 ml) and Pd(OH)$_2$/C (150 mg) was added. The resultant mixture was stirred under hydrogen atmosphere for 1 h. The catalyst was filtered off and the solvents were evaporated. The residue was dissolved in a mixture of CH$_2$Cl$_2$ (2 ml) and DMF (1 ml) and then linker reagent 8 (30 mg, 0.1 mmol, solution in 0.1 ml of CH$_2$Cl$_2$) and Et$_3$N (50 μl) were added. After 1 h the mixture was diluted with toluene, concentrated and subjected to silica gel column chromatography (toluene/Me$_2$CO, 4:1) to give 10 (132 mg, 89%) as a colorless foam. $^1$H NMR data (500 MHz, CDCl$_3$): δ 2.38 (s, 3H, CH$_3$COS), 3.53 (s, 2H, CH$_2$S); $^{13}$C NMR data (125 MHZ, CDCl$_3$): δ 30.2 (CH$_3$COS), 32.9 (CH$_2$S).

A mixture of the protected pentasaccharide 10 (100 mg, 0.017 mmol), EtOH (5 ml) and N$_2$H$_4$.H$_2$O (0.5 ml) was stirred under reflux for 1 h and then concentrated and subjected to gel permeation chromatography (TSK gel Toyopearl HW 40S, 2.5×40 cm) in 0.1M aqueous AcOH to furnish pentasaccharide 11 (32 mg, 93%). $^1$H NMR data (500 MHz, D$_2$O): δ 7.17 (s, 1H, CH=N); $^{13}$C NMR data (125 MHZ, D$_2$O): δ 134.6 (C=N—NH$_2$), 167.4 (C(O)—CH=N). Mass-spectra: calculated for C$_{35}$H$_{67}$N$_8$O$_{22}$ 951.438 [M+H]$^+$, experimental 951.448 [M+H]$^+$.

Example 6

Study of Applicability of Linking Reagent 12 for the Preparation of Ligands for Further Conjugation with Protein Scheme 5. Synthesis of the ligands.. a: 1) H$_2$, Pd(OH)$_2$/C, MeOH/THF 2) 12, Et$_3$N, CH$_2$Cl$_2$; b: N$_2$H$_4$•H$_2$O, EtOH, Δ

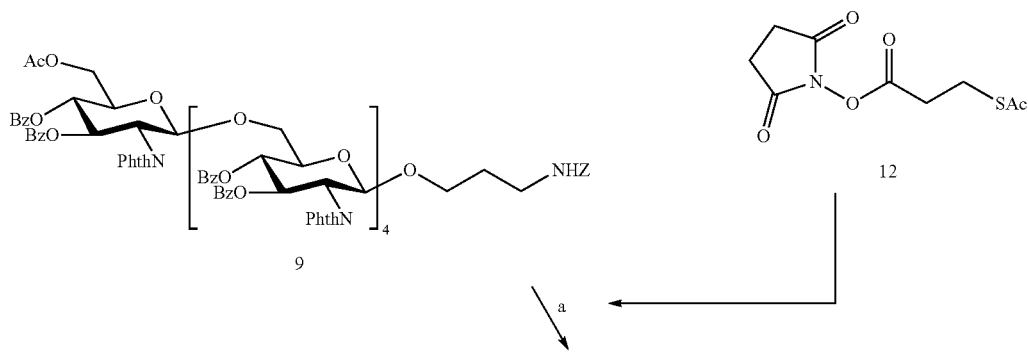

Pentasaccharide 9 (100 mg, 0.017 mmol) (M. L. Gening, Y. E. Tsvetkov, G. B. Pier, N. E. Nifantiev, <<Synthesis of oligo-β(1→6)-glucosamines corresponding to the fragments of the surface polysaccharide of *Staphylococcus aureus*>> *Carbohydr. Res.* 342 (2007), 567-575) was dissolved in a mixture of MeOH (1.5 ml), THF (3 ml) and 1M HCl (0.1 ml) and Pd(OH)$_2$/C (150 mg) was added. The resultant mixture was stirred under hydrogen atmosphere for 1 h. The catalyst was filtered off and the solvents were evaporated. The residue was dissolved in a mixture of CH$_2$Cl$_2$ (2 ml) and DMF (1 ml) and then linker reagent 12 (15 mg, 0.061 mmol, solution in 0.1 ml of CH$_2$Cl$_2$) and Et$_3$N (50 μl) were added. After 1 h the mixture was diluted with toluene, concentrated and subjected to silica gel column chromatography (toluene/Me$_2$CO, 4:1) to give 13 (87 mg, 85%) as a colorless foam. $^1$H NMR data (500 MHz, CDCl$_3$): δ 2.33 (s, 3H, CH$_3$COS), 2.52 (m, 2H, COCH$_2$), 3.15 (t, 2H, J 7.6, CH$_2$S); $^{13}$C NMR data (125 MHZ, CDCl$_3$): δ 25.2 (CH$_3$COS), 29.2 (COCH$_2$), 35.9 (CH$_2$S).

A mixture of the protected pentasaccharide 13 (80 mg, 0.015 mmol), EtOH (5 ml) and N$_2$H$_4$.H$_2$O (0.5 ml) was stirred under reflux for 1 h and then concentrated and subjected to gel permeation chromatography (TSK gel Toyopearl HW 40S, 2.5×40 cm) in 0.1M aqueous AcOH to give complex mixture of nonidentified products.

Example 7

Preparation of the Conjugate of Tetanus Toxoid with Ligand 6—"TT-9NH$_2$"

Step 1. Protein Modification.

Tetanus toxoid (4 mg in 120 stock solution) was diluted with 400 µl of pH 7.2 buffer (0.1 M sodium phosphate, 0.15 M NaCl, 10 mM EDTA), the solution of SBAP (2.6 mg) in DMSO (80 µl) was added and the mixture was incubated for 2 h at RT. Unreacted SBAP was removed using PD-10 column in pH 8.0 running buffer (0.1 M sodium phosphate, 0.15 M NaCl, 10 mM EDTA) and resultant 3.5 ml solution of modified protein was concentrated to 400 µl.

protein with the Bradford assay (M. M. Bradford, 1976, *Analytical Biochem.* 72:248-254). According to these assays, conjugate TT-9NH$_2$ contains 74 carbohydrate ligands per protein molecule (x=74).

Example 8

Preparation of the Conjugate of tetanus toxoid with Ligand 7—"TT-9NAc"

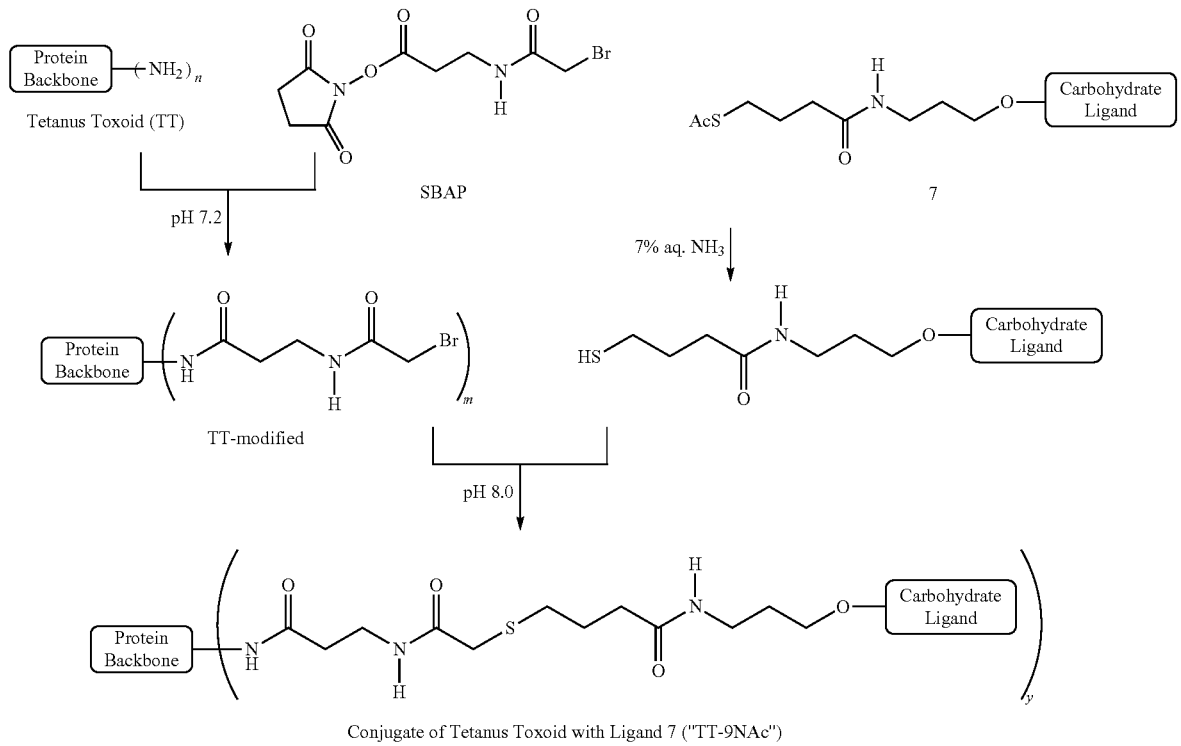

Conjugate of Tetanus Toxoid with Ligand 7 ("TT-9NAc")

Step 2. Disulfide Reduction.

Immobilized TCEP Disulfide Reducing Gel (200 µl of 50% slurry in water) was centrifuged, an excess of water was removed and disulfide 6 (1.5 mg in 100 µl of pH 8.0 buffer (0.1 M sodium phosphate, 0.15 M NaCl, 10 mM EDTA)) was added. After incubation on a rotor rack at room temperature for 45 min, the solution of SH-derivative was separated from the gel by centrifugation and immobilized TCEP was washed with the same pH 8.0 buffer (3×100 µl).

Step 3. Conjugation.

The solution of the ligand obtained in Step 2 (400 µl in pH 8.0 buffer) was immediately combined with modified protein (400 µl in pH 8.0 buffer, Step 1.) and stirred overnight at room temperature. After this time, the conjugate was separated from uncoupled components by gel filtration on Superose 6 prep-grade column. Fractions, containing TT-9NH$_2$ conjugate were pooled, concentrated and stored frozen at −20° C.

Chemical Analysis of Conjugate.

Conjugate was analyzed for its contents of oligosaccharides using hexosamine assay described by Smith and Gilkerson (R. L. Smith and E. Gilkerson. 1979 *Analytical Biochem.* 98: 478-480) with compounds 6 as a standard and for Step 1. Protein Modification.

TT was modified with SBAP as described above for conjugate TT-9NH$_2$.

Step 2. S-Acetyl Deprotection.

Nonasaccharide 7 (2.1 mg) was dissolved in 200 µl of 7% aqueous NH$_3$ solution, the mixture was kept at room temperature for 1 hour and then lyophilized.

Step 3. Conjugation.

Lyophilized oligosaccharide was immediately dissolved in 400 µl of pH 8.0 buffer (0.1 M sodium phosphate, 0.15 M NaCl, 10 mM EDTA) and mixed with 400 µl of TT-modified solution in the same buffer. Reaction mixture was stirred overnight at room temperature. After this time, the conjugate was separated from uncoupled components by gel filtration on Superose 6 prep-grade column. Fractions containing TT-9NAc conjugate were pooled, concentrated and stored frozen at −20° C.

Chemical Analysis of Conjugate.

The analysis was performed the same way as for conjugate TT-9NH$_2$ (Example 7) and revealed that conjugate TT-9NAc contains 71 carbohydrate ligands per protein molecule (y=71).

Example 9

Antibody Production Using Oligosaccharide Conjugates

Methods.

Rabbits were immunized subcutaneously with 10 µg polysaccharide equivalent of nonaglucosamine (i.e., 9 linked monomers) conjugated to tetanus toxoid (TT) twice, one week apart, with an equivalent volume of Specol adjuvant. On the third week, rabbits were immunized three times (i.e., on Monday, Wednesday and Friday) with 10 µg PS-equivalent IV in saline. After the last immunization, rabbits were rested for two weeks and blood was taken every two weeks. Data in this presentation incorporate results from the first (bleed 1) and second (bleed 2) sera obtained post-immunization Results.

FIGS. 1A and B show the data relating to binding of antisera raised to non-acetylated nona-glucosamine (9GlcNH$_2$) to PNAG (A) or dPNAG (B) from *S. aureus*. dPNAG used in this experiment was about 15% acetylated. However, it is to be understood that the level of acetylation may range from 0-40%. The data show that the antisera bound comparably to both PNAG and dPNAG.

Figure 2A:
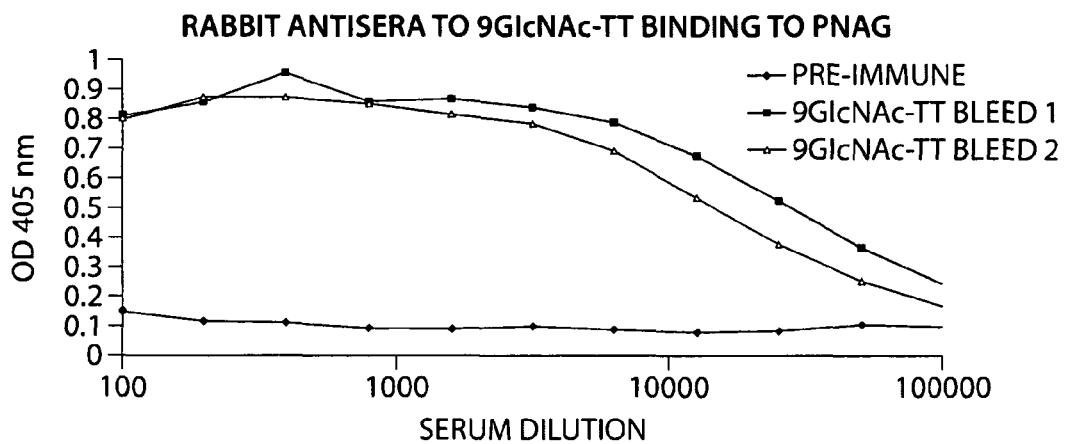
FIGS. 2A and B are graphs showing binding of antisera raise to fully acetylated nona-glucosamine (9GlcNAc) to PNAG or dPNAG from *S. aureus*.
Figure 2B:
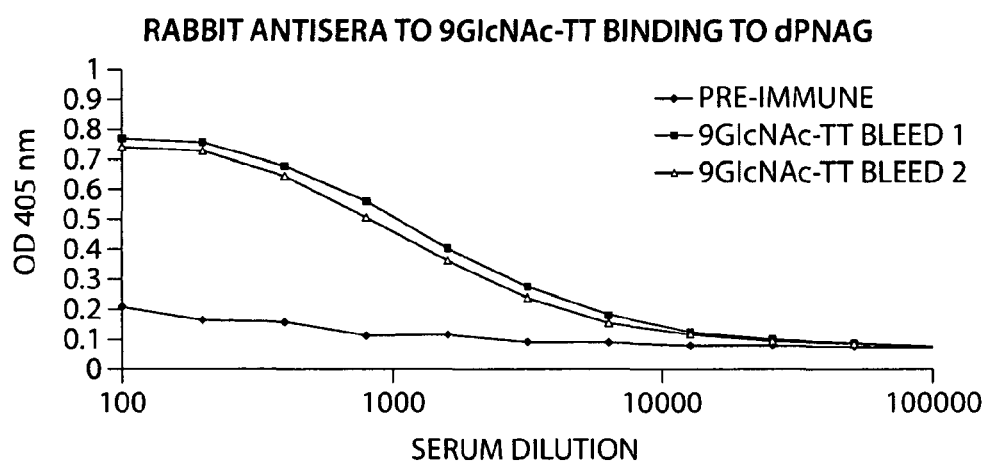

FIGS. 2A and B show the data relating to binding of antisera raise to fully acetylated non-glucosamine (9GlcNAc) to PNAG or dPNAG from *S. aureus*. The data show that the antisera bound better to highly acetylated PNAG than to dPNAG.

Figure 3A:
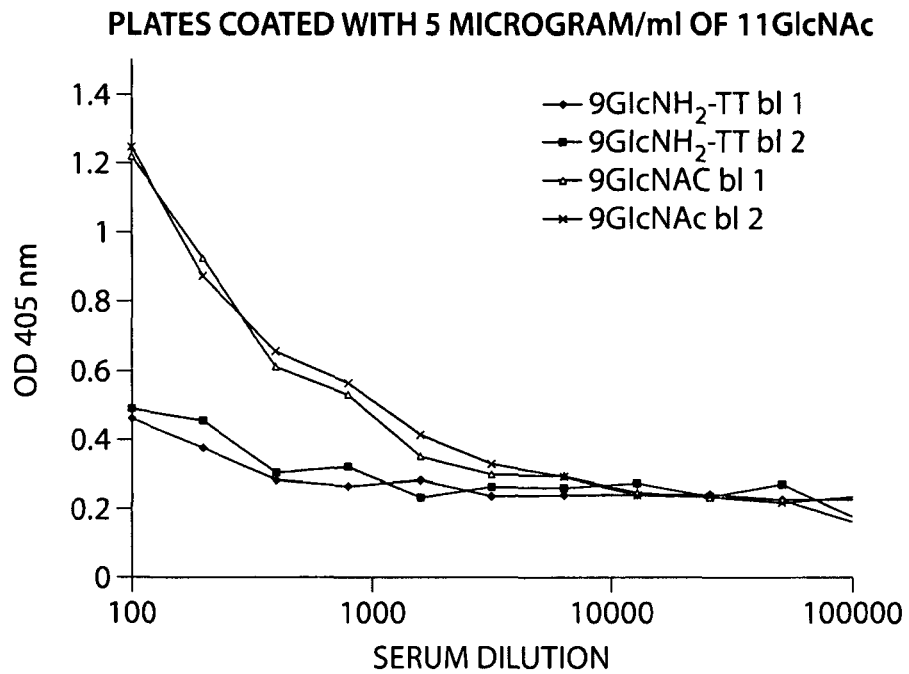
FIGS. 3A and B are graphs showing binding of antisera raised to conjugated 9GlcNAc or 9GlcNH$_2$ to 11GlcNAc or 11GlcNH$_2$.
Figure 3B:
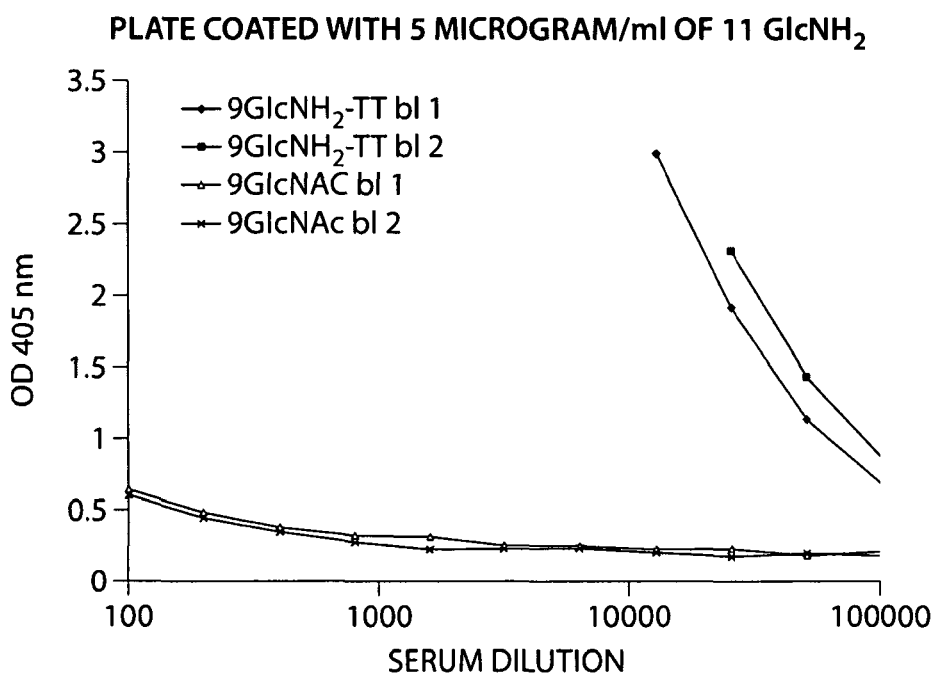

FIGS. 3A and B show the data relating to the binding of antisera raised to TT-conjugated 9GlcNAc or 9GlcNH$_2$ to unconjugated 11 GlcNAc or 11GlcNH$_2$. The data show that the antiserum raised against acetylated 9GlcNAc bound better to acetylated 11GlcNAc than did the antiserum raised against non-acetylated 9GlcNH$_2$. The opposite was true for binding to 9GlcNH$_2$, as antisera to 9GlcNH$_2$-TT conjugate was off-scale at serum dilutions of less than 6400.

Figure 4:
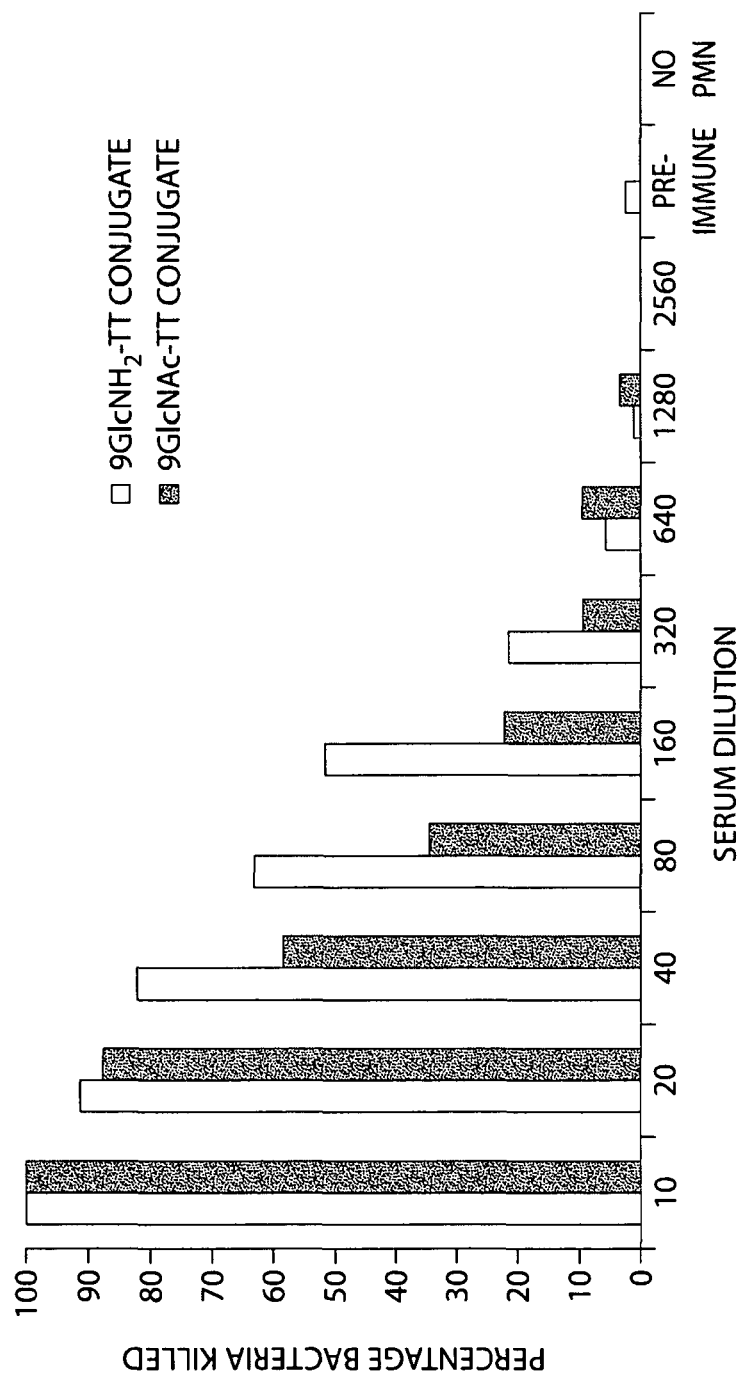
FIG. 4 is a graph showing killing of S. aureus strain MN8 bacteria using an antisera raised in two rabbits, one received the 9GlcNH$_2$-TT conjugate and the second received the 9GlcNAc-TT conjugate with the antiserum taken 2 weeks after the last injection of vaccine.
Figure 5:
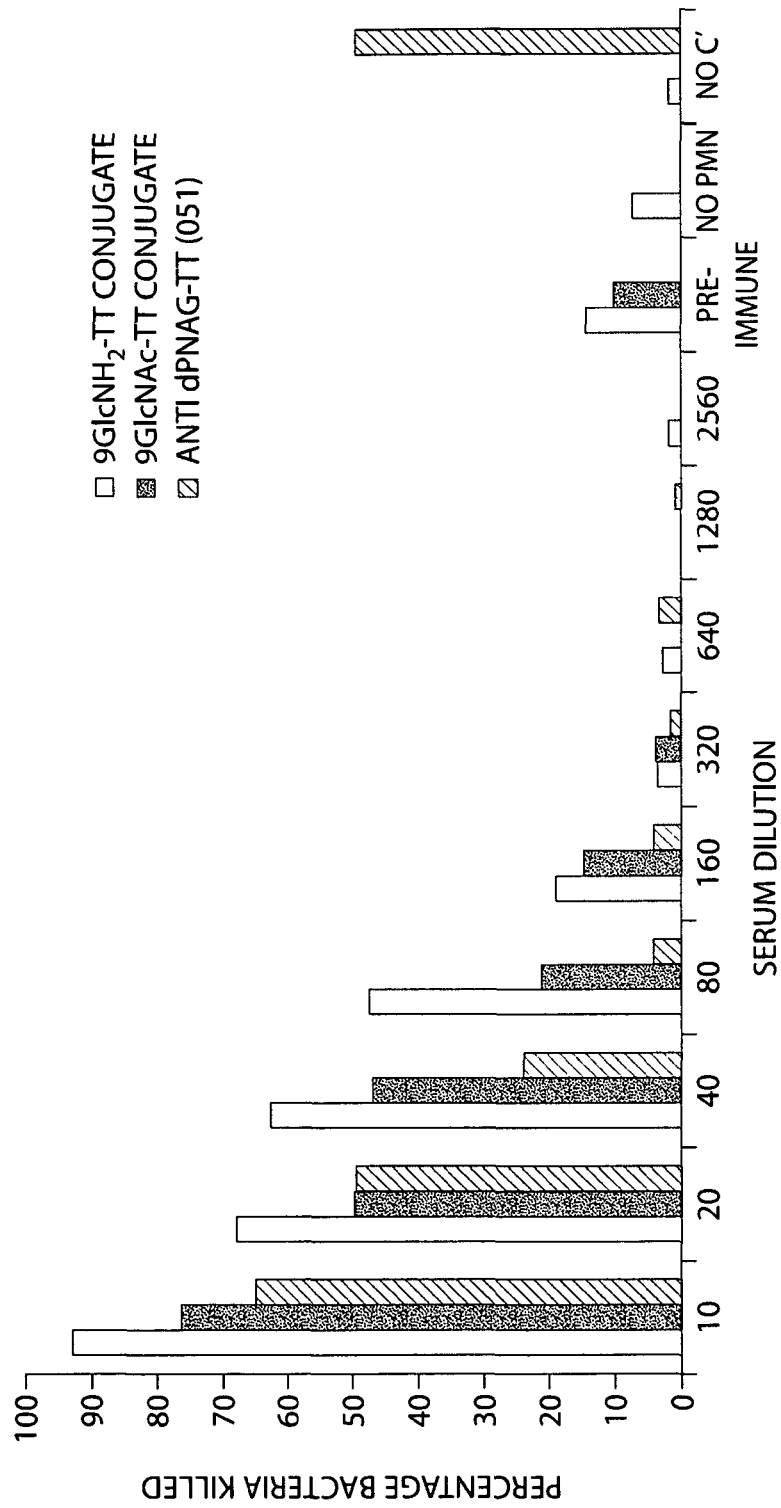
FIG. 5 is a graph showing killing of S. aureus strain MN8 bacteria using an antisera raised in two rabbits, one of which received the 9GlcNH$_2$-TT conjugate and the second received the 9GlcNAc-TT conjugate with the antiserum taken 4 weeks after the last injection of vaccine and also shows, for comparison, killing of the same bacteria by an antiserum raised to a conjugate vaccine consisting of the dPNAG molecule of ~100 kDa conjugated to tetanus toxoid (TT) and further labeled (051).
Figure 6:
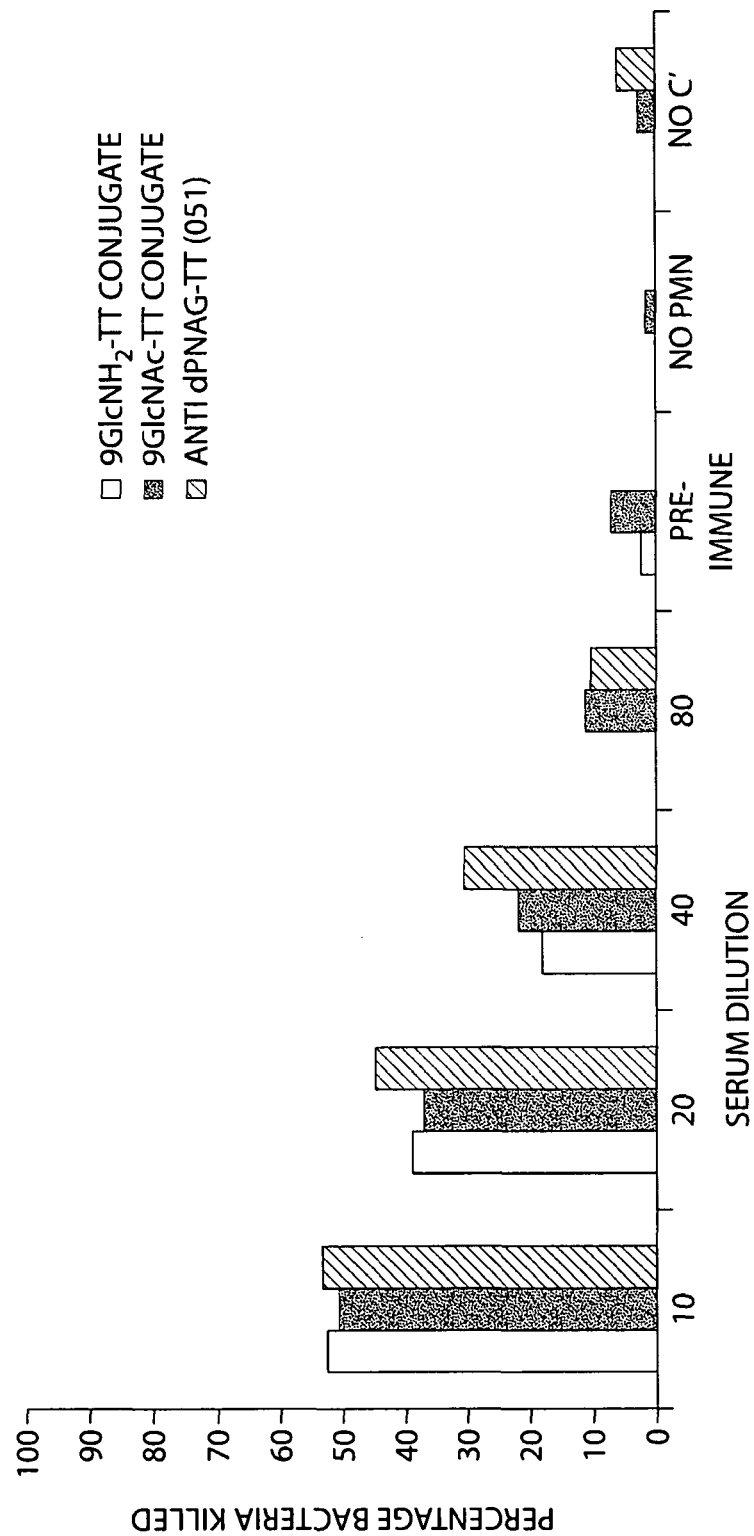
FIGS. 6-8 are graphs comparing the killing of S. aureus strains (FIGS. 6 and 8, LAC (NT, USA300)
Figure 7:
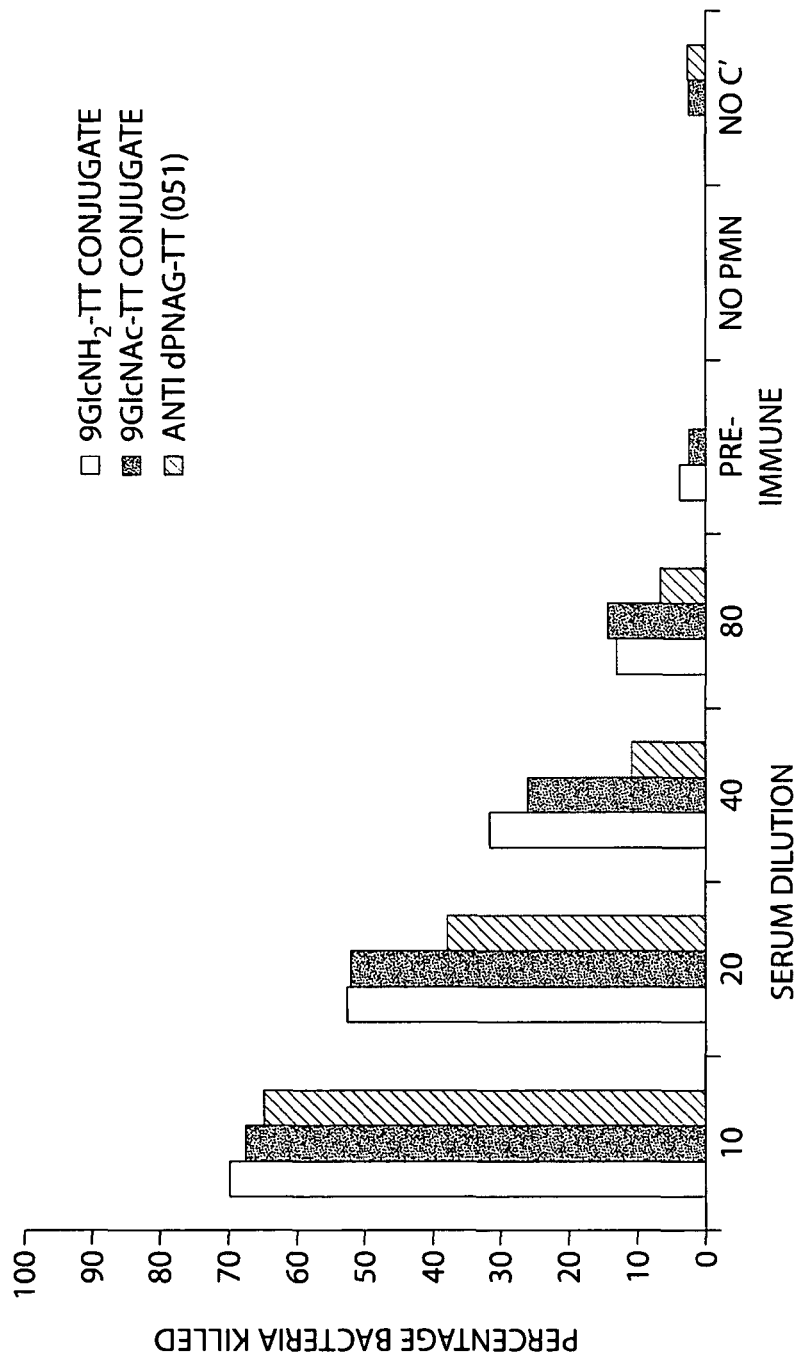
Figure 8:
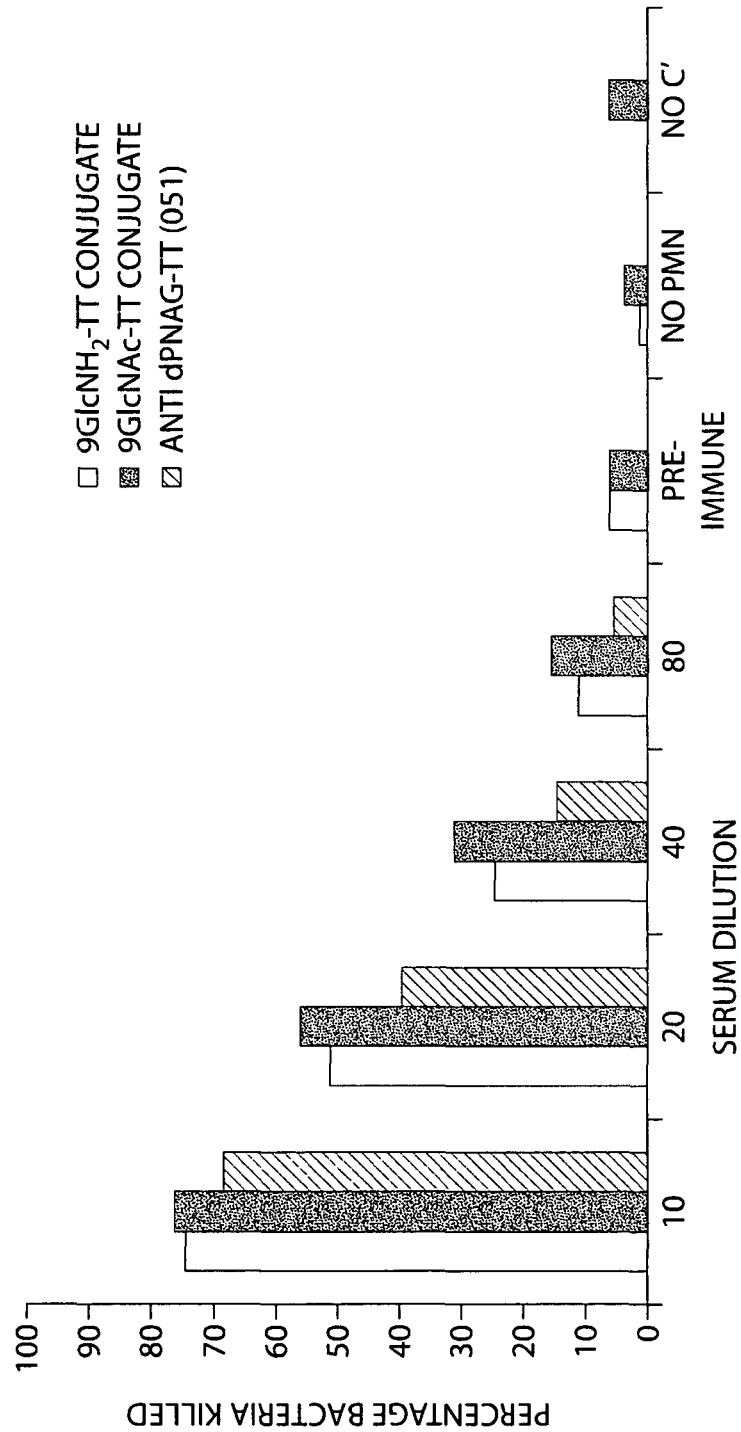

FIGS. 4 and 5 show results using antisera from bleed 1 against *S. aureus* MN8 and two USA300 strains. FIG. 4 compares the killing of *S. aureus* MN8 (CP8) by rabbit antisera (referred to as "bleed 1") to fully acetylated or non-acetylated 9-mer oligoglucosamine conjugated to tetanus toxoid (TT). FIG. 5 compares the killing of *S. aureus* MN8 by rabbit antisera (bleed 1) to fully acetylated or non-acetylated 9-mer oligoglucosamine conjugated to TT. Anti-dPNAG-TT conjugate antiserum was used as a comparator. FIG. 6 compares the killing of *S. aureus* LAC (NT, USA300) by rabbit sera (bleed 1) to fully acetylated or non-acetylated 9-mer oligoglucosamine conjugated to TT. FIG. 7 compares the killing of *S. aureus* SF8300 (NT, USA300) by rabbit sera (bleed 1) to fully acetylated or non-acetylated 9-mer oligoglucosamine conjugated to TT. FIG. 8 compares the killing of *S. aureus* LAC (NT, USA300) by rabbit sera (bleed 1) to fully acetylated or non-acetylated 9-mer oligoglucosamine conjugated to TT. In general, serum raised to 9GlcNH$_2$-TT demonstrated the best overall activity but in most assays was only slightly better than serum raised to 9GlcNAc-TT.

FIGS. 9-16 show killing data resulting from the use of bleed 2 sera. Rabbit anti dPNAG-TT control used as comparator for strains MN8, SF8300 and LAC. Goat anti-dPNAG-TT was used as a comparator for Newman (CP5), PS80 (CP8) and the isogenic strains Reynolds CP5, Reynolds nontypable and Reynolds CP8.

Figure 9:
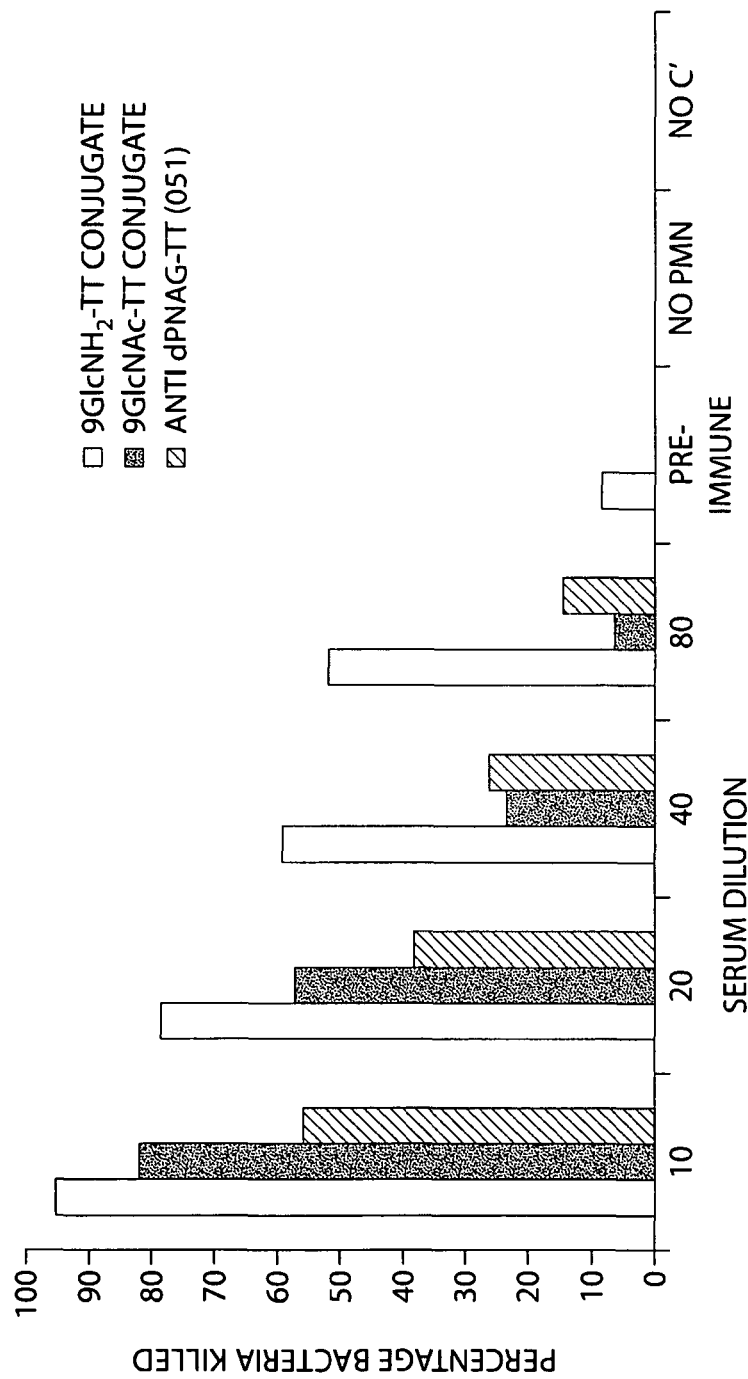
FIGS. 9-16 are graphs comparing the killing of S. aureus strains (FIG. 9, MN8 (capsular polysaccharide (CP) 8)
Figure 10:
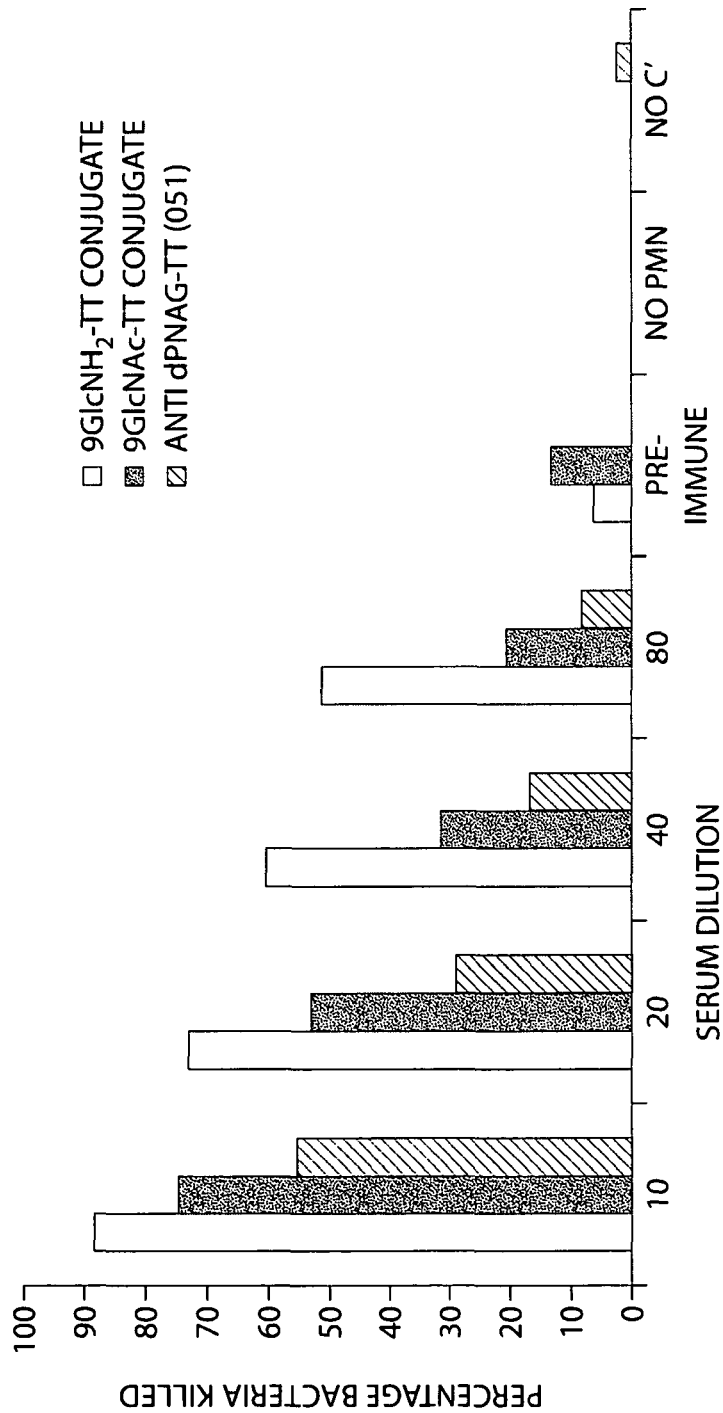
Figure 11:
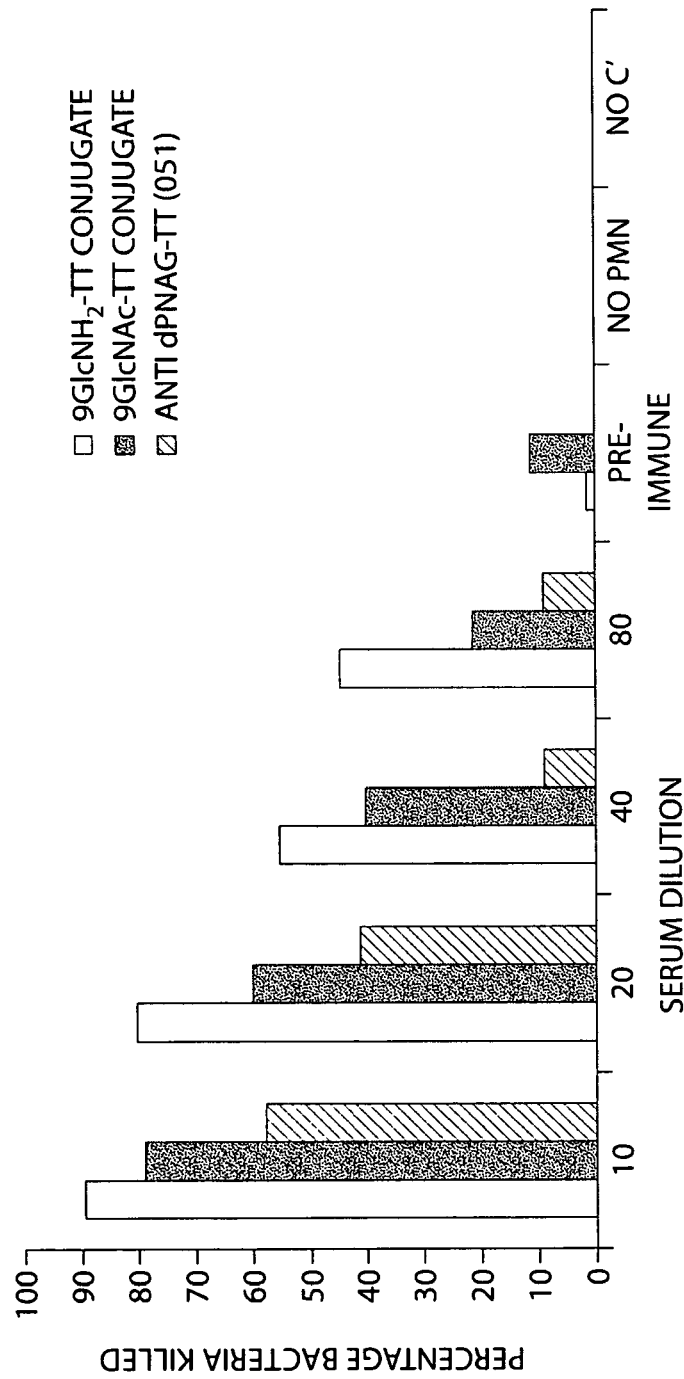
Figure 12:
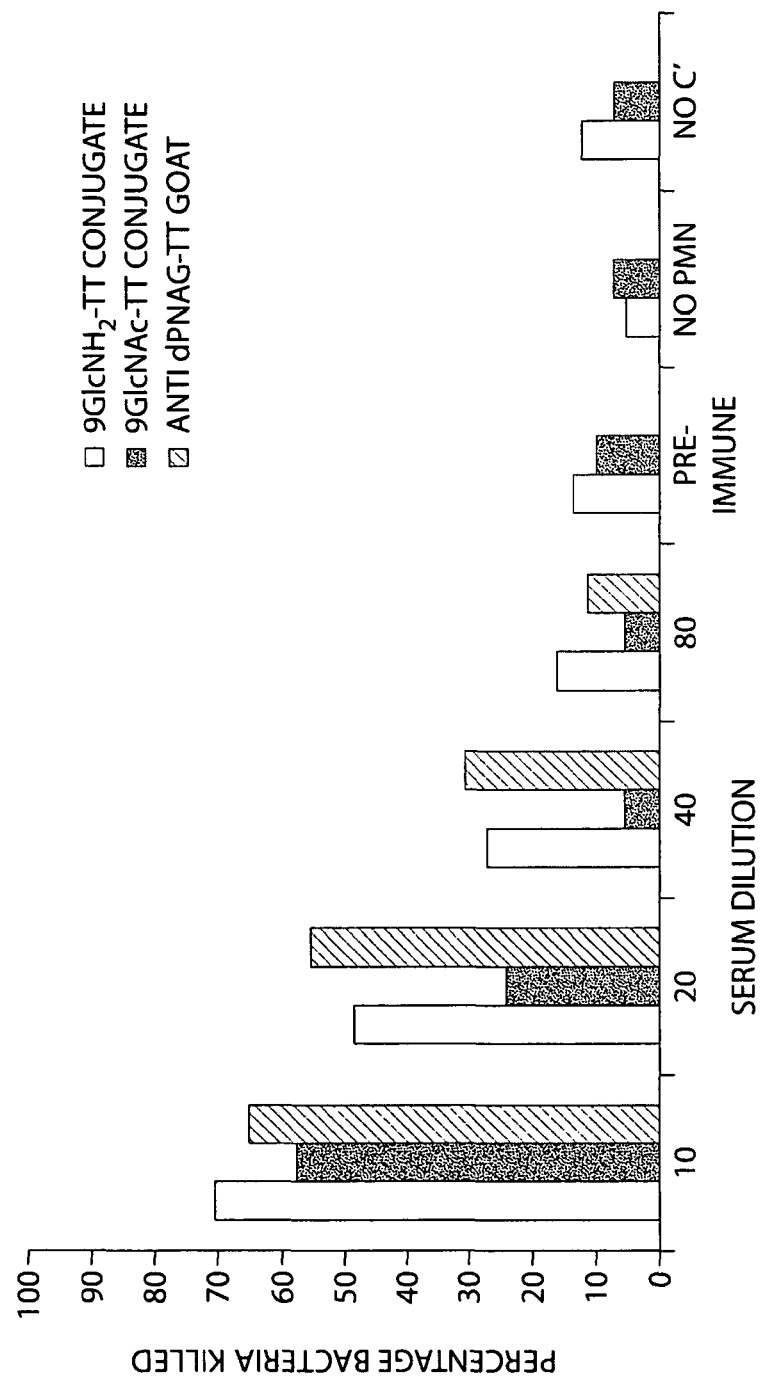
Figure 13:
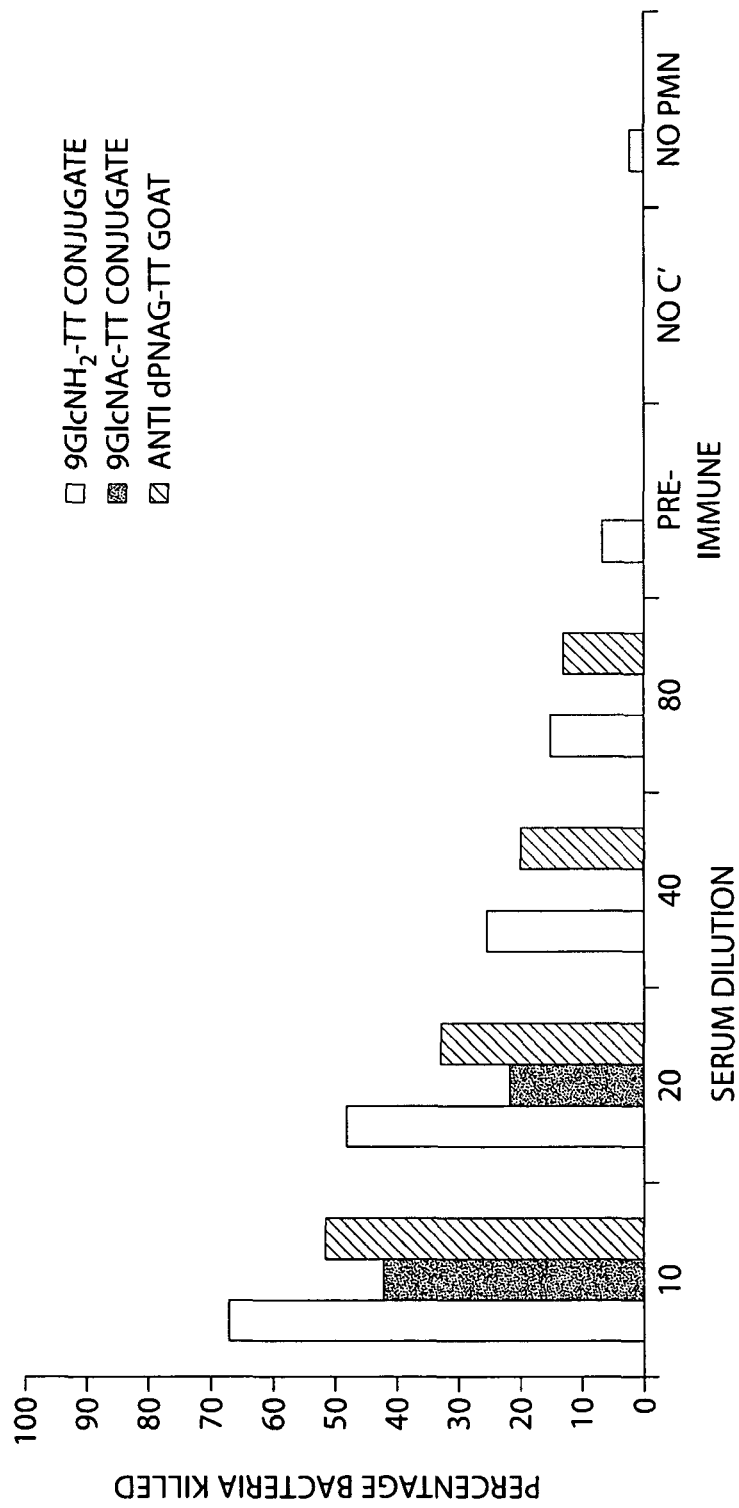
Figure 14:
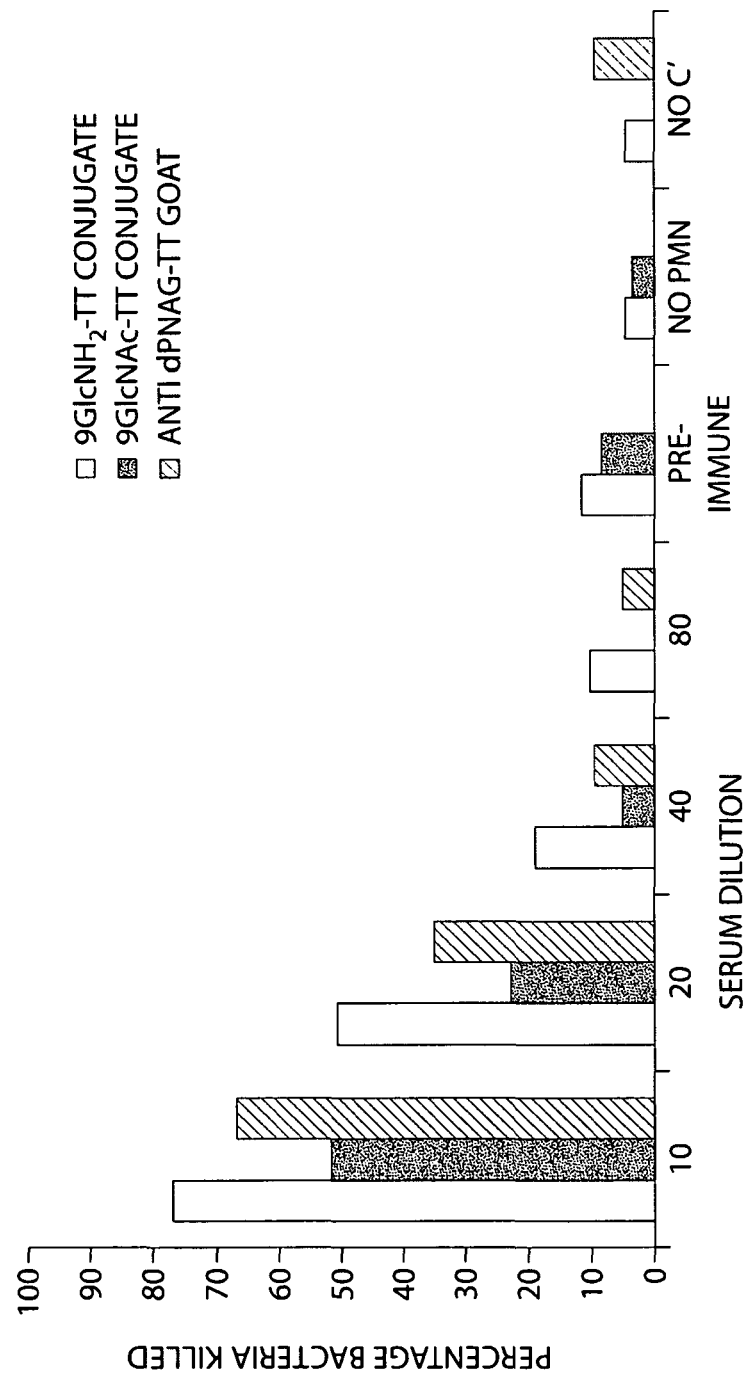
Figure 15:
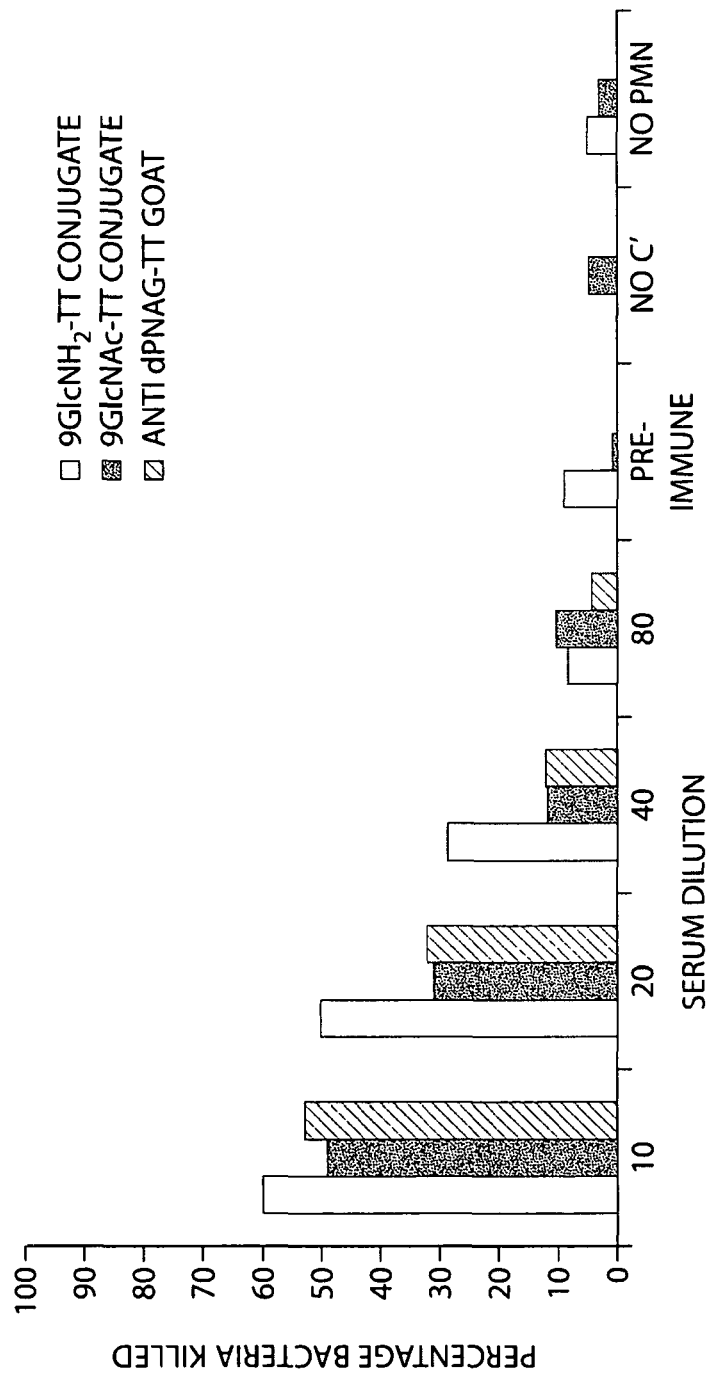
Figure 16:
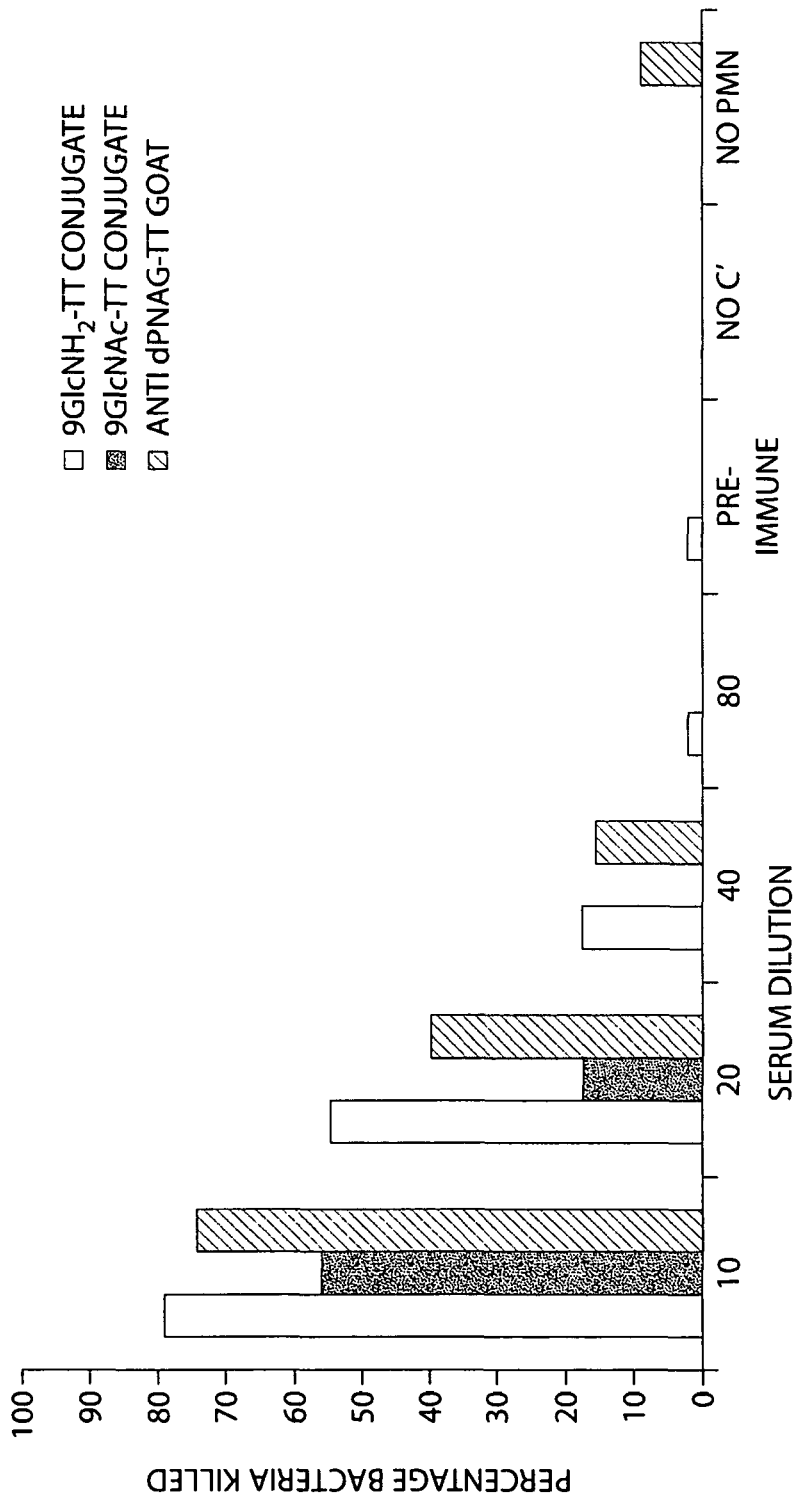

FIG. 9 compares the killing of *S. aureus* MN8 (CP8) by rabbit sera (bleed 2) to fully acetylated or non-acetylated 9-mer oligoglucosamine conjugated to TT. FIG. 10 compares the killing of *S. aureus* LAC (NT. USA300) by rabbit sera (bleed 2) to fully acetylated or non-acetylated 9-mer oligoglucosamine conjugated to TT. FIG. 11 compares the killing of *S. aureus* SF8300 (NT, USA300) by rabbit sera (bleed 2) to fully acetylated or non-acetylated 9-mer oligoglucosamine conjugated to TT. FIG. 12 compares the killing of *S. aureus* Newman (CP5) by rabbit sera (bleed 2) to fully acetylated or non-acetylated 9-mer oligoglucosamine conjugated to TT. FIG. 13 compares the killing of *S. aureus* PS80 by rabbit sera (bleed 2) to fully acetylated or non-acetylated 9-mer oligoglucosamine conjugated to TT. FIG. 14 compares the killing of *S. aureus* Reynolds (CP5) by rabbit sera (bleed 2) to fully acetylated or non-acetylated 9-mer oligoglucosamine conjugated to TT. FIG. 15 compares the killing of *S. aureus* Reynolds (non-typable) by rabbit sera (bleed 2) to fully acetylated or non-acetylated 9-mer oligoglucosamine conjugated to TT. FIG. 16 compares the killing of *S. aureus* Reynolds (CP8) by rabbit sera (bleed 2) to fully acetylated or non-acetylated 9-mer oligoglucosamine conjugated to TT.

Generally, a higher degree of killing was achieved using antisera raised to the oligosaccharide conjugates than with antiserum raised to dPNAG-TT. Killing of strains LAC and SF8300 was better with bleed 2 sera as compared with bleed 1 sera even though the ELISA binding curves are similar. Using bleed 2, a greater difference in killing using the antisera raised to 9GlcNH$_2$ is seen as compared to lysis using serum raised to 9GlcNAc.

Example 10

Rabbit Antisera and Opsonic Killing of *E. coli*

Figure 16A:
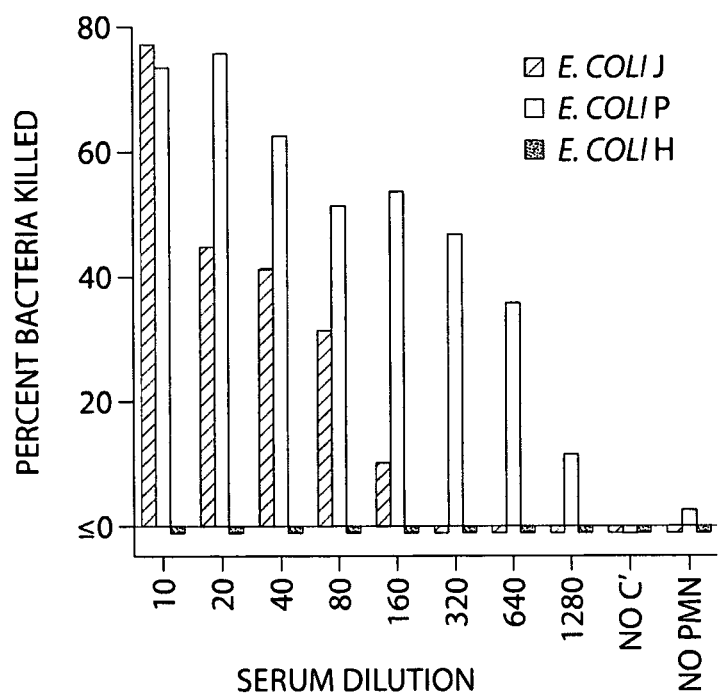
FIG. 16A is a graph showing the killing of two PNAG-positive (E. coli J and E. coli P) but not PNAG-negative (E. coli H) E. coli strains by rabbit antisera to 9GlcNH$_2$-TT obtained 6 weeks after the last immunization.

Rabbit antibodies in post-immunization rabbit antisera (as described above) mediated opsonic killing of two *E. coli* strains previously shown to produce PNAG, but not a third strain lacking the pga genes encoding the biosynthetic enzymes for PNAG in *E. coli* (FIG. 16A).

Example 11

Mouse Skin Abscess Models

Figure 17:
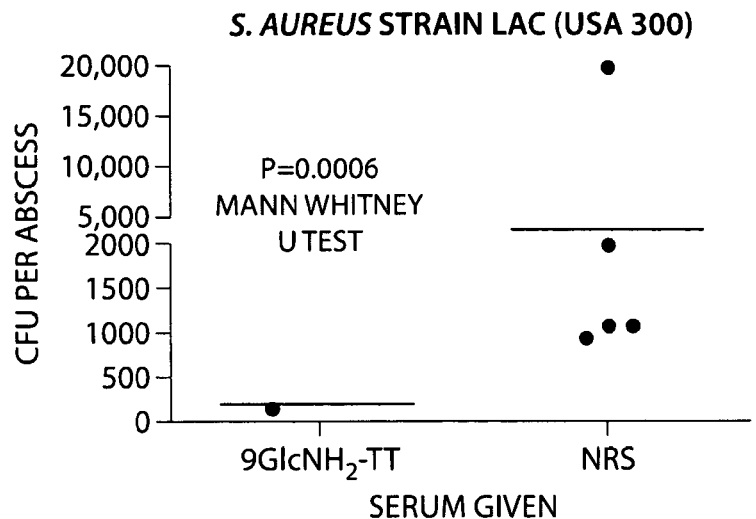
FIGS. 17, 18 and 19 are graphs showing the results of an in vivo study relating to prevention of S. aureus skin abscess infection after immunization with an antiserum raised to the 9-mer nonacetylated oligoglucosamine conjugated to TT (9GlcNH$_2$-TT, bleed 2) and administered to mice 24 hr prior to infection with $2 \times 10^4$ (FIG. 18), $2 \times 10^5$ (FIG. 19) or $2 \times 10^6$ (FIG. 20) CFU of S. aureus strain LAC.
Figure 18:
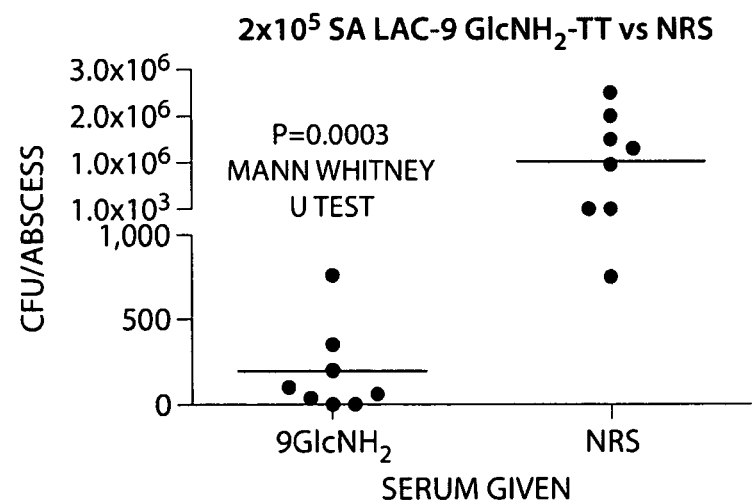
Figure 19:
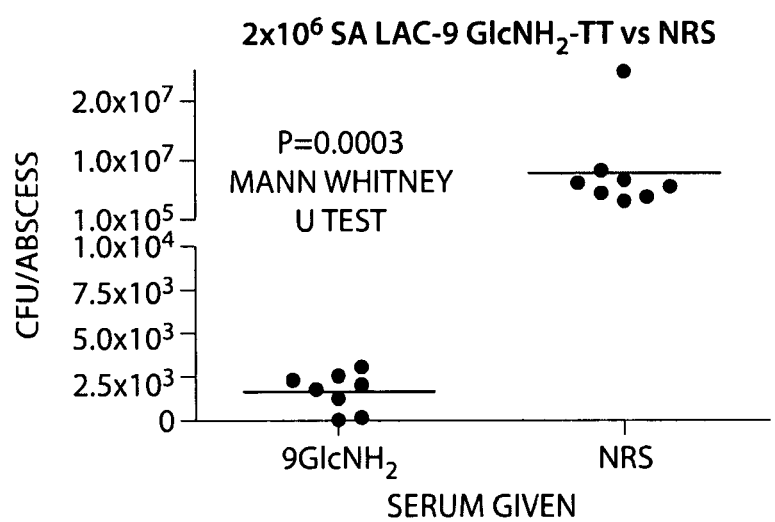
Figure 20:
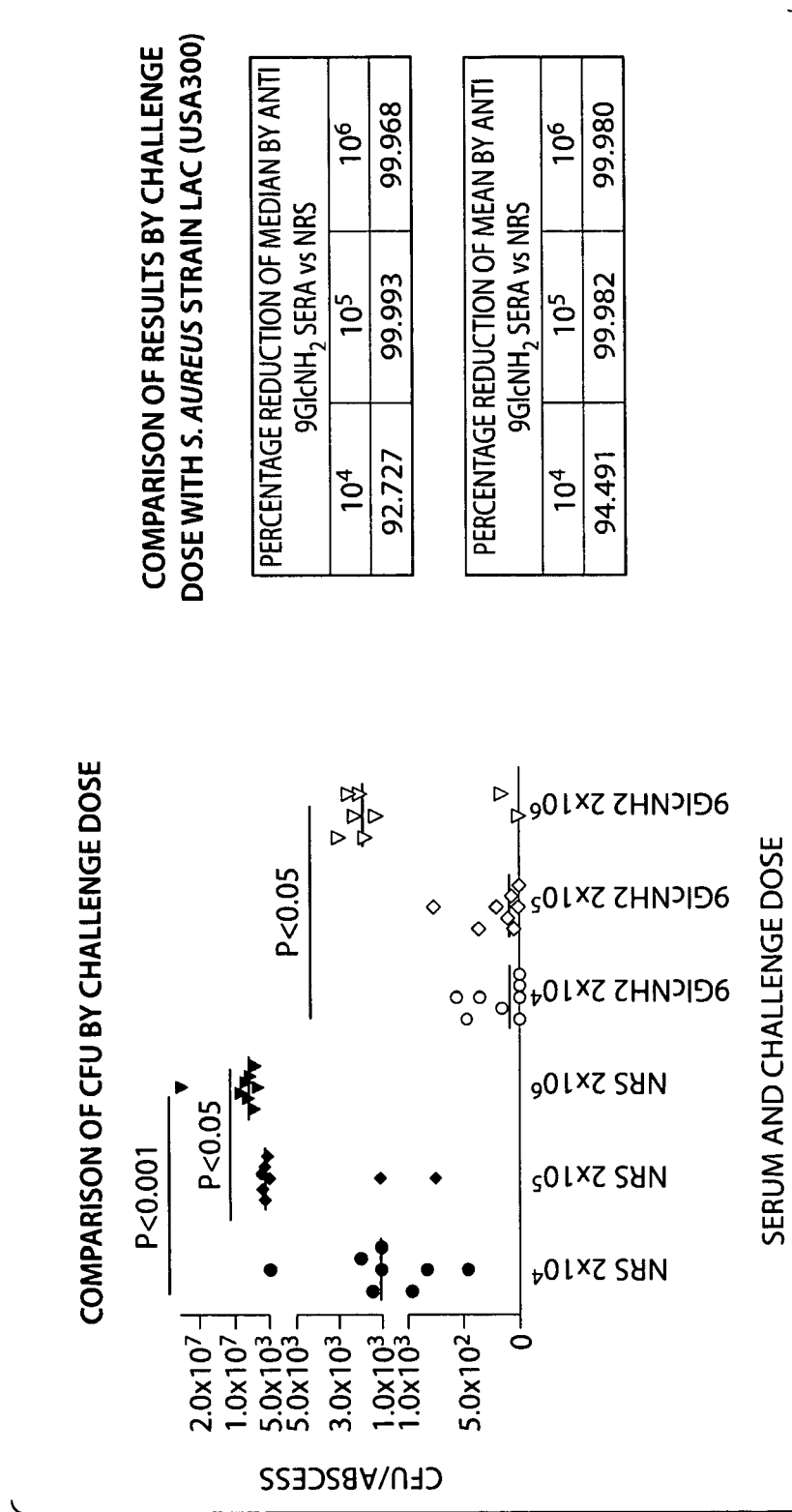
FIG. 20 is a summary of the results in FIGS. 17-19.

FIGS. 17, 18 and 19 show the results of an in vivo study using a mouse skin abscess model and challenge with *S. aureus* strain LAC (USA300). Antisera raised to 9GlcNH$_2$ demonstrated protective efficacy against an *S. aureus* LAC (USA300) skin infection. Group 1 (labeled 9GlcNH$_2$-TT) was administered 0.2 ml of 9GlcNH$_2$-TT antiserum (bleed 2) intraperitoneally 24 hours prior to infection. Group 2 (labeled NRS) was administered 0.2 ml of normal rabbit serum (NRS) 24 hours prior to infection. Mice were infected with $2 \times 10^4$ CFU (FIG. 17), $2 \times 10^5$ CFU (FIG. 19), or $2 \times 10^6$ CFU (FIG. 20) in a 100 µl subcutaneous injection (per abscess) with microdex beads (10 g/ml). *S. aureus* LAC strain was grown in TSB overnight, then washed and added to the microdex beads prior to administration. After 72 hours, each abscess was excised, resuspended in 1 ml of TSB, homogenized, diluted, and then 100 µl of homogenate were plated along with serial dilutions. The lower limit of detection was 10 CFU/abscess. FIGS. 17, 18 and 19 show that the number of CFU per abscess was greatly reduced in mice administered the 9GlcNH$_2$-TT antiserum as compared to the normal rabbit serum. FIG. 20 summarizes the results of FIGS. 18-20 showing that at every dose of *S. aureus*, the mice administered 9GlcNH$_2$ were better protected against the *S. aureus* challenge.

Figure 21:
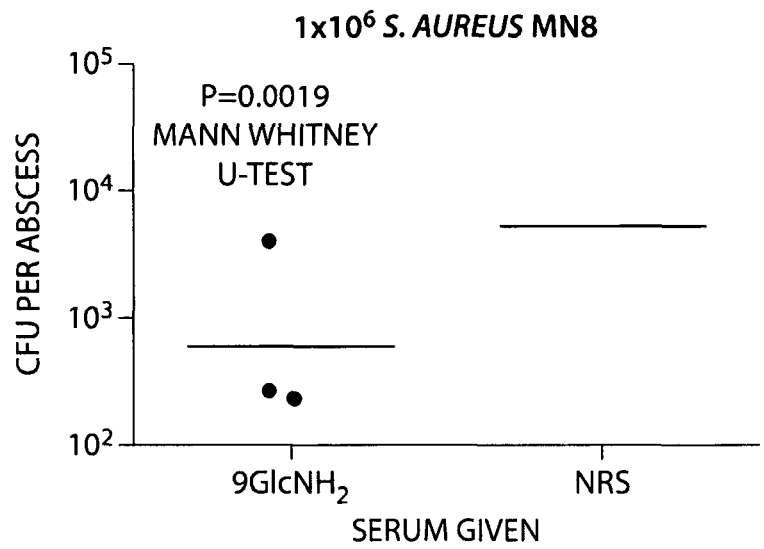
FIGS. 21, 22 and 23 are graphs showing the results of in vivo studies relating to prevention of S. aureus abscess infection after immunization with an antiserum raised to the 9-mer nonacetylated oligoglucosamine and administered to mice prior to infection with $1 \times 10^6$ CFU S. aureus MN8 (FIG. 21), $4 \times 10^6$ CFU S. aureus Newman (FIG. 22), and $4 \times 10^6$ CFU S. aureus NewmanΔica and $1.5 \times 10^6$ CFU S. aureus MN8Δica (FIG. 23).
Figure 22:
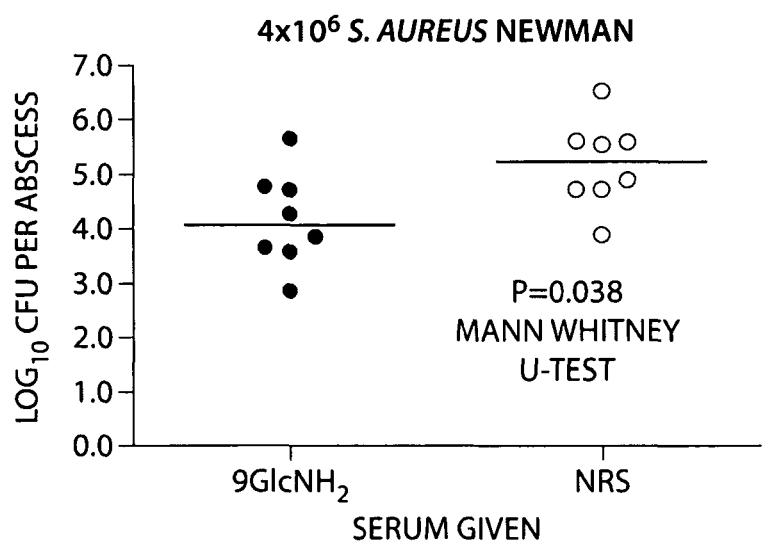

FIGS. 21 and 22 show the results of two in vivo studies using the same mouse skin abscess model and procedures described in the preceding paragraph but the challenge strains are two additional S. aureus strains, MN8 and Newman. Mice were infected with 1×10⁶ CFU of strain MN8 (FIG. 21) or 4×10⁶ CFU of strain Newman (FIG. 22) in a 100 µl subcutaneous injection (per abscess) with microdex beads (10 g/ml). FIGS. 21 and 22 show that the number of CFU per abscess was significantly reduced in mice administered the 9GlcNH$_2$-TT antiserum as compared to the normal rabbit serum.

Figure 23:
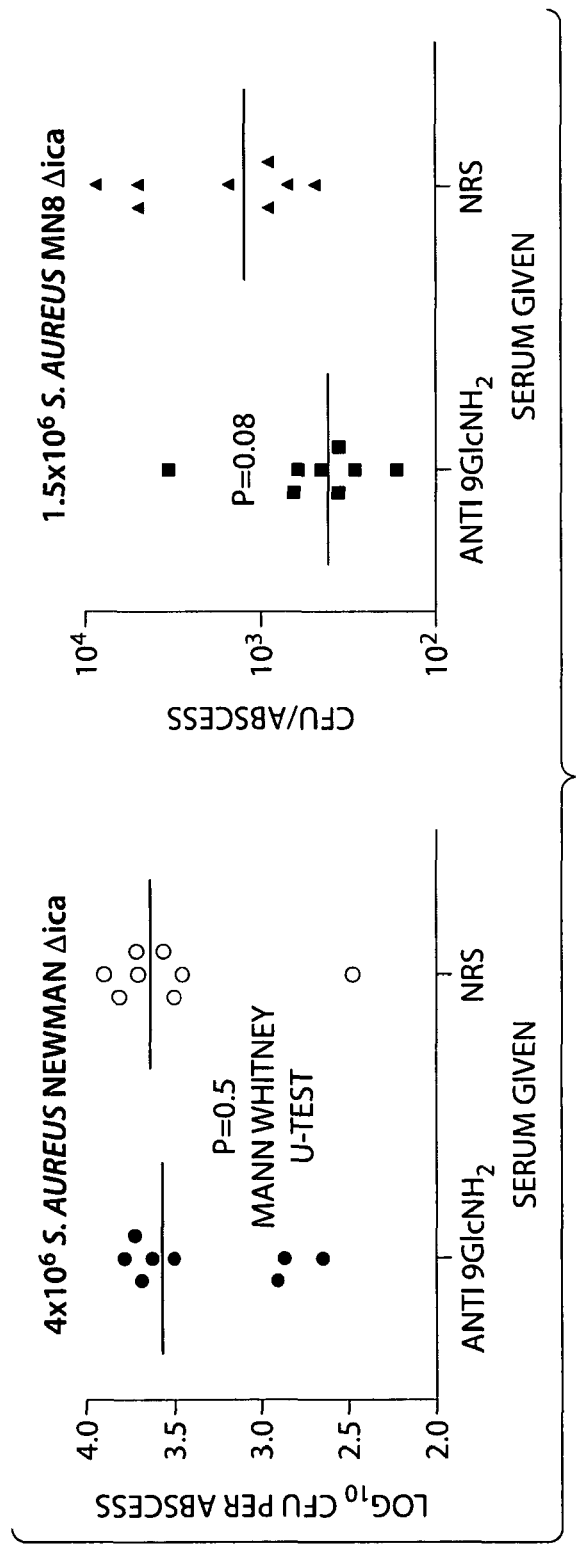

FIG. 23 shows the inability of the antiserum raised to the 9GlcNH$_2$-TT conjugate vaccine to significantly (P>0.05) reduce the CFU/abscess of S. aureus strains MN8Δica and NewmanΔica. These two strains have had the ica genetic locus removed and can no longer synthesize the PNAG surface polysaccharide. In the absence of the PNAG antigen, the antibody to the 9GlcNH$_2$ oligosaccharide cannot provide any protective immunity to S. aureus skin infections.

Example 12

Protective Efficacy against E. coli peritonitis

The protective efficacy of antibody to 9GlcNH$_2$-TT was tested in a lethal peritonitis model of E. coli infection. This antibody protected all immunized mice against infection caused by two PNAG-positive E. coli isolates (Table 1, UTI strains J and P) whereas all controls receiving NRS did not survive. There was no protection afforded by antibody to 9GlcNH$_2$-TT antiserum against PNAG-negative E. coli strain H.

TABLE 1

Protective efficacy of antibody to 9GlcNH$_2$-TT against lethal peritonitis caused by E. coli.

| Challenge E. coli strain | Number of survivors out of total mice | | P value (Fisher's exact test) |
|---|---|---|---|
| | Anti-9GlcNH$_2$TT | NRS$^a$ | |
| J (PNAG⁺) | 8/8 | 0/8 | 0.0002 |
| P (PNAG⁺) | 8/8 | 0/8 | 0.0002 |
| H (PNAG⁻) | 0/8 | 0/8 | 1.0 |

$^a$NRS: normal rabbit serum

Discussion of Results

Using the fully non-acetylated, synthetic GlcNH$_2$-TT conjugate vaccines, it has been found according to the invention that no acetates are required for generating high levels of opsonic and protective antibodies in animals, that conjugating a molecule as small as five GlcNH$_2$-monomers in size is sufficient for a robust immune response, and that these antibodies readily bind to highly N-acetylated PNAG, poorly acetylated dPNAG and the non-acetylated oligosaccharides. These protective antibodies will therefore bind to naturally occurring PNAG regardless of its composition, including its level of acetylation.

The invention further contemplates producing vaccines that comprise multiple antigens including the non-acetylated oligosaccharides of the invention. The synthesis of GlcNH$_2$-oligomers with a reducing end linker containing a reactive sulfhydryl group suggests that vaccines targeting microbes that make PNAG could be made more effective by conjugating the GlcNH$_2$-oligosaccharides to microbial proteins that function as virulence factors and vaccine antigens. For example, the LcrV protein of Y. pestis is a target for protection against plague (Garmory et al. Vaccine 22:947-57 (2004); Overheim et al. Infect. Immun. 73:5152-9 (2005); Quenee et al. Infect. Immun. 76:2025-2036 (2008)) but serologic variants of this protein are known among strains of Y. pestis circulating in central Asia (Anisimov et al. Clin. Microbiol. Rev. 17:434-464 (2004)), making it possible such strains could evade immunity engendered by a single LcrV vaccine component. As PNAG is expressed by Y. pestis, conjugating GlcNH$_2$-oligomers to LcrV might enhance the protective coverage of a plague vaccine. This approach to vaccine production is attractive since the synthetic version of dPNAG oligosaccharides can be produced fairly inexpensively and, importantly, will not have any other microbial contaminants.

Overall these findings indicate that small sized oligomers of beta(1→6)-linked glucosamine conjugated to a carrier protein can induce high titers of opsonic antibody that is also protective against experimental S. aureus skin infection and lethal peritonitis due to E. coli.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition comprising
an oligosaccharide-carrier conjugate comprising an oligosaccharide conjugated to a carrier through a linker that is

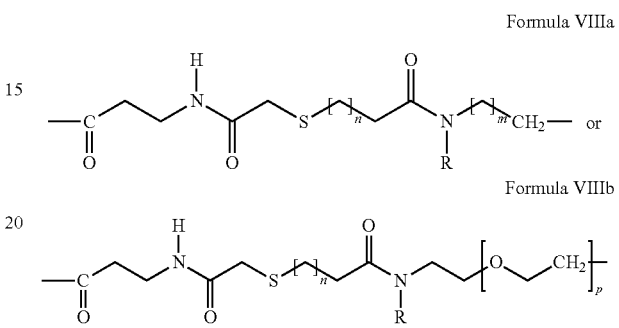

wherein n is greater than 1, m is a number selected from 1 to 10, p is a number selected from 1 to 20, and R is H or an alkyl group, and
wherein the linker is O-linked to the oligosaccharide and N-linked to the carrier, the oligosaccharide is a β-1,6-linked glucosamine and the carrier is a peptide or protein.

2. The composition of claim 1, wherein the carrier is tetanus toxoid.

3. The composition of claim 1, wherein the composition has an oligosaccharide to carrier ratio of 1:1, 2:1, 3:1, 4:1, 5:1, 6:1, 7:1, 8:1, 9:1, 10:1, 20:1, 30:1, 40:1, 50:1, 60:1, 70:1, 80:1, 90:1 or 100:1.

4. The composition of claim 1, wherein the oligosaccharide is 2-20 monomers in length.

5. The composition of claim 1, wherein the oligosaccharide is 5-11 monomers in length.

6. The composition of claim 1, wherein the oligosaccharide is 7, 9 or 11 monomers in length.

7. The composition of claim 1, wherein the oligosaccharide is 0-40% acetylated.

8. The composition of claim 1, further comprising a pharmaceutically acceptable carrier.

9. The composition of claim 1, further comprising an adjuvant.

10. The composition of claim 1, further comprising an anti-bacterial agent.

* * * * *

UNITED STATES PATENT AND TRADEMARK OFFICE
CERTIFICATE OF CORRECTION

| | | |
|---|---|---|
| PATENT NO. | : 8,492,364 B2 | Page 1 of 1 |
| APPLICATION NO. | : 13/055178 | |
| DATED | : July 23, 2013 | |
| INVENTOR(S) | : Pier et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 88 days.

Signed and Sealed this
Third Day of March, 2015

Michelle K. Lee
*Deputy Director of the United States Patent and Trademark Office*